(12) United States Patent
Duncan et al.

(10) Patent No.: US 11,653,769 B2
(45) Date of Patent: May 23, 2023

(54) METHODS AND SYSTEMS OF SPRING MODULES FOR AN ADJUSTABLE SLEEPING SYSTEM

(71) Applicant: SLEEP TECHNOLOGIES, LLC, Harlingen, TX (US)

(72) Inventors: Robert B. Duncan, Harlingen, TX (US); Matthew Hayward, Richardson, TX (US); Heather D. Benoit, Austin, TX (US); Mark W. Foohey, Austin, TX (US); J. Kevin Gentry, Austin, TX (US); Samuel C. Scudder, Webberville, TX (US)

(*) Notice: Subject to any disclaimer, the term of this patent is extended or adjusted under 35 U.S.C. 154(b) by 174 days.

(21) Appl. No.: 16/714,153

(22) Filed: Dec. 13, 2019

(65) Prior Publication Data
US 2020/0187665 A1    Jun. 18, 2020

Related U.S. Application Data

(60) Provisional application No. 62/779,629, filed on Dec. 14, 2018.

(51) Int. Cl.
  *A47C 23/28*    (2006.01)
  *A47C 23/30*    (2006.01)
  (Continued)

(52) U.S. Cl.
  CPC .......... *A47C 27/061* (2013.01); *A47C 23/002* (2013.01); *A47C 27/045* (2013.01);
  (Continued)

(58) Field of Classification Search
  CPC ..... A47C 23/28; A47C 23/30; A47C 23/0435; A47C 27/061
  See application file for complete search history.

(56) References Cited

U.S. PATENT DOCUMENTS

| 6,433 | A | 5/1849 | Webster |
| 12,111 | A | 12/1854 | Wright |

(Continued)

FOREIGN PATENT DOCUMENTS

| CA | 1265262 A | 1/1990 |
| CA | 65629 S | 3/1990 |

(Continued)

OTHER PUBLICATIONS

International Searching Authority, Search Report and Written Opinion for related PCT/US2019/066380, dated Feb. 19, 2020; 8 pages.

(Continued)

*Primary Examiner* — David R Hare
*Assistant Examiner* — Ifeolu A Adeboyejo
(74) *Attorney, Agent, or Firm* — Dickinson Wright, PLLC

(57) ABSTRACT

Spring modules for an adjustable sleeping system. At least some of the example embodiments are spring modules comprising: a spring rail, and a plurality of adjustable spring assemblies spaced along the length of the spring rail. Each adjustable spring assembly may comprise: a motor with a stator coupled to the spring rail, a lead screw coupled to the rotor of the motor, and the lead screw extending above an upper surface of the spring rail, a spring plate coupled to the lead screw, and a main spring coupled to the spring plate. Thus, the weight or force carried by each adjustable spring assembly along the spring rail is separately adjustable by a bed controller.

14 Claims, 13 Drawing Sheets

(51) Int. Cl.
  *A47C 27/06* (2006.01)
  *A47C 27/045* (2006.01)
  *A47C 23/00* (2006.01)
  *A47C 31/12* (2006.01)
  *A61H 23/00* (2006.01)
  *A61H 23/02* (2006.01)
  *A47C 23/04* (2006.01)
  *A61B 5/00* (2006.01)

(52) U.S. Cl.
  CPC .......... *A47C 27/065* (2013.01); *A47C 31/123* (2013.01); *A61H 23/004* (2013.01); *A61H 23/0254* (2013.01); *A47C 23/04* (2013.01); *A47C 27/064* (2013.01); *A61B 5/6891* (2013.01); *A61H 2201/5061* (2013.01); *A61H 2203/0443* (2013.01)

(56) References Cited

U.S. PATENT DOCUMENTS

| | | | |
|---|---|---|---|
| 82,457 A | 9/1868 | Ward et al. | |
| 118,351 A | 8/1871 | Dunarray | |
| 207,776 A | 9/1878 | Roswall | |
| 218,927 A | 8/1879 | Bury | |
| 277,541 A | 5/1883 | Bowers | |
| 322,382 A | 7/1885 | Keith | |
| 414,292 A | 11/1889 | Clevett | |
| 656,411 A | 8/1900 | Leggett | |
| 729,021 A | 5/1903 | Van Cise et al. | |
| 754,097 A | 3/1904 | Shannon | |
| 977,253 A | 11/1910 | Ade | |
| 1,276,760 A | 8/1918 | Hines | |
| 2,112,702 A * | 3/1938 | Loibl | A61G 7/1057 |
| | | | 5/934 |
| 2,314,361 A | 1/1941 | Meutsch | |
| 2,315,706 A * | 4/1943 | Hopkes | A47C 23/30 |
| | | | 267/88 |
| 2,558,288 A * | 6/1951 | Backus | A47C 23/0435 |
| | | | 5/248 |
| 2,595,072 A * | 4/1952 | Gottschalk | A47C 23/0435 |
| | | | 5/256 |
| 2,630,585 A * | 3/1953 | Reese | A47C 23/0435 |
| | | | 5/248 |
| 3,088,132 A | 5/1963 | Vogel | |
| 3,656,190 A | 4/1972 | Regan et al. | |
| 4,175,549 A | 11/1979 | Hamer | |
| 4,222,137 A * | 9/1980 | Usami | A47C 23/0435 |
| | | | 5/697 |
| 4,597,118 A | 7/1986 | Mis | |
| 4,644,593 A | 2/1987 | O'Brien | |
| 4,644,597 A | 2/1987 | Walker | |
| 4,766,597 A | 8/1988 | Olshansky | |
| 4,766,628 A | 8/1988 | Walker | |
| 4,788,729 A | 12/1988 | Walker | |
| 4,799,276 A * | 1/1989 | Kadish | A61G 7/0573 |
| | | | 137/901 |
| D300,194 S | 3/1989 | Walker | |
| 4,890,344 A | 1/1990 | Walker | |
| 4,897,890 A | 2/1990 | Walker | |
| 4,908,895 A | 3/1990 | Walker | |
| 4,991,244 A | 2/1991 | Walker | |
| 5,144,706 A | 9/1992 | Walker | |
| 5,170,522 A | 12/1992 | Walker | |
| 5,170,552 A | 12/1992 | Swiderski et al. | |
| 5,305,738 A | 4/1994 | Shimizu | |
| 5,509,154 A | 4/1996 | Shafer et al. | |
| 5,523,040 A | 6/1996 | Krouskop | |
| 5,542,907 A | 8/1996 | Chou | |
| 5,553,836 A * | 9/1996 | Ericson | B60G 17/021 |
| | | | 267/221 |
| 5,564,140 A | 10/1996 | Shoenhair et al. | |
| 5,625,914 A * | 5/1997 | Schwab | A47C 23/002 |
| | | | 5/652 |
| 5,642,546 A | 7/1997 | Shoenhair | |
| 5,904,172 A | 5/1999 | Gifft et al. | |
| 6,098,223 A | 8/2000 | Larson | |
| 6,146,342 A | 11/2000 | Glen | |
| 6,161,231 A | 12/2000 | Kraft et al. | |
| 6,202,239 B1 | 3/2001 | Ward et al. | |
| 6,219,863 B1 | 4/2001 | Loberg et al. | |
| 6,397,419 B1 | 6/2002 | Mechache | |
| 6,471,197 B1 | 10/2002 | Denk et al. | |
| 6,487,738 B1 * | 12/2002 | Graebe | A47C 23/043 |
| | | | 267/82 |
| 6,560,804 B2 | 5/2003 | Wise et al. | |
| 6,686,711 B2 | 2/2004 | Rose et al. | |
| 6,708,357 B2 | 3/2004 | Gaboury et al. | |
| 6,721,981 B1 * | 4/2004 | Greenhalgh | A47C 31/123 |
| | | | 5/264.1 |
| 6,763,541 B2 | 7/2004 | Mahoney et al. | |
| 6,804,848 B1 | 10/2004 | Rose | |
| 6,832,397 B2 | 12/2004 | Gaboury et al. | |
| 6,883,191 B2 | 4/2005 | Gaboury et al. | |
| 7,069,610 B1 | 7/2006 | Chai | |
| 7,107,642 B2 | 9/2006 | Wong et al. | |
| 7,270,222 B1 * | 9/2007 | Aymar | F16F 9/461 |
| | | | 188/285 |
| 7,676,872 B2 * | 3/2010 | Block | G01L 5/0038 |
| | | | 5/933 |
| 7,856,895 B2 * | 12/2010 | Syassen | G01B 5/207 |
| | | | 73/862.541 |
| 7,865,988 B2 | 1/2011 | Koughan et al. | |
| 7,934,277 B1 * | 5/2011 | Shu | A47C 23/0435 |
| | | | 5/936 |
| 7,941,882 B1 * | 5/2011 | Strozer | A47C 31/003 |
| | | | 5/693 |
| 8,328,287 B2 * | 12/2012 | Hsu | A47C 7/40 |
| | | | 297/452.1 |
| 8,341,786 B2 | 1/2013 | Oexman et al. | |
| D698,338 S | 1/2014 | Ingham et al. | |
| 8,672,842 B2 | 3/2014 | Kenalty et al. | |
| 8,672,853 B2 | 3/2014 | Young | |
| 8,752,222 B2 * | 6/2014 | Papaioannou | G05D 16/20 |
| | | | 5/657 |
| 8,769,747 B2 | 7/2014 | Mahoney et al. | |
| 8,844,079 B2 | 9/2014 | Skinner et al. | |
| 8,844,943 B2 * | 9/2014 | Kim | B60G 99/002 |
| | | | 280/5.514 |
| 8,973,183 B1 | 3/2015 | Palashewski et al. | |
| 9,131,782 B1 | 9/2015 | Baker | |
| 9,138,065 B2 * | 9/2015 | Chandler | A47C 27/15 |
| 9,314,386 B1 | 4/2016 | Boyd | |
| 9,836,930 B2 | 12/2017 | De Luca | |
| 9,924,813 B1 | 3/2018 | Basten et al. | |
| 9,933,775 B2 * | 4/2018 | Saavedra | G05B 19/106 |
| 9,955,795 B2 | 5/2018 | Krenik | |
| 10,010,187 B1 * | 7/2018 | Mencio | A47C 7/35 |
| 10,334,957 B2 * | 7/2019 | Edling | B60N 2/7011 |
| 10,416,031 B2 | 9/2019 | Hsu et al. | |
| 10,561,253 B2 | 2/2020 | Tsem et al. | |
| 10,588,420 B1 * | 3/2020 | Krenik | A47C 19/027 |
| 11,021,029 B2 * | 6/2021 | Harrison | B60G 11/265 |
| 2002/0184711 A1 | 12/2002 | Mahoney et al. | |
| 2004/0231057 A1 * | 11/2004 | Sabin | A47C 31/08 |
| | | | 5/716 |
| 2005/0204475 A1 | 9/2005 | Schmitz et al. | |
| 2005/0235417 A1 | 10/2005 | Koughan et al. | |
| 2005/0257883 A1 | 11/2005 | Anagnostopoulos | |
| 2006/0253994 A1 | 11/2006 | Sprinks et al. | |
| 2008/0035156 A1 | 2/2008 | Hyde et al. | |
| 2008/0052830 A1 | 3/2008 | Koughan et al. | |
| 2008/0077020 A1 | 3/2008 | Young et al. | |
| 2008/0052837 A1 | 5/2008 | Blumberg | |
| 2008/0276377 A1 * | 11/2008 | Hsu | A47C 23/0435 |
| | | | 5/727 |
| 2009/0038080 A1 | 2/2009 | Grigg | |
| 2010/0043148 A1 | 2/2010 | Rose et al. | |
| 2010/0170043 A1 | 7/2010 | Young et al. | |
| 2010/0174198 A1 | 7/2010 | Young et al. | |
| 2010/0174199 A1 | 7/2010 | Young et al. | |
| 2010/0218315 A1 | 9/2010 | Hyde et al. | |

(56) References Cited

U.S. PATENT DOCUMENTS

| | | |
|---|---|---|
| 2010/0257675 A1 | 10/2010 | DeMoss |
| 2010/0325810 A1 | 12/2010 | Dahlin et al. |
| 2011/0010014 A1 | 1/2011 | Oexman et al. |
| 2011/0144455 A1 | 6/2011 | Young et al. |
| 2011/0296621 A1 | 12/2011 | McKenna |
| 2011/0296622 A1 | 12/2011 | Hsu |
| 2011/0314612 A1 | 12/2011 | Hsu |
| 2012/0042454 A1* | 2/2012 | Viberg .............. A47C 27/062 5/727 |
| 2012/0056458 A1* | 3/2012 | Hsu ................ A47C 7/345 297/311 |
| 2012/0110744 A1* | 5/2012 | Hsu ................ A47C 23/0435 5/697 |
| 2012/0186019 A1 | 7/2012 | Rawls-Meehan |
| 2013/0000049 A1* | 1/2013 | Hsu ................ A47C 23/0435 5/710 |
| 2013/0089717 A1 | 4/2013 | Loffelmann et al. |
| 2013/0283530 A1* | 10/2013 | Main ................ A47C 31/123 5/600 |
| 2013/0340175 A1 | 12/2013 | Stevens et al. |
| 2014/0007656 A1 | 1/2014 | Mahoney |
| 2014/0059775 A1 | 3/2014 | Khanzadian |
| 2014/0114486 A1 | 4/2014 | Ponnuhamy |
| 2014/0137332 A1 | 5/2014 | McGuire et al. |
| 2014/0137337 A1 | 5/2014 | DeFranks et al. |
| 2014/0182061 A1 | 7/2014 | Zaiss et al. |
| 2014/0250597 A1 | 9/2014 | Chen et al. |
| 2014/0257571 A1 | 9/2014 | Chen et al. |
| 2014/0259417 A1 | 9/2014 | Nunn et al. |
| 2014/0259418 A1 | 9/2014 | Nunn et al. |
| 2014/0259419 A1 | 9/2014 | Stusynski et al. |
| 2014/0259431 A1 | 9/2014 | Fleury et al. |
| 2014/0259433 A1 | 9/2014 | Nunn et al. |
| 2014/0259434 A1 | 9/2014 | Nunn et al. |
| 2014/0277611 A1 | 9/2014 | Nunn et al. |
| 2014/0277778 A1 | 9/2014 | Nunn et al. |
| 2014/0277822 A1 | 9/2014 | Nunn et al. |
| 2015/0007393 A1 | 1/2015 | Palashewski |
| 2015/0008710 A1 | 1/2015 | Young et al. |
| 2015/0025327 A1 | 1/2015 | Young et al. |
| 2015/0108188 A1 | 4/2015 | MacLachlan et al. |
| 2015/0182033 A1 | 7/2015 | Brosnan et al. |
| 2015/0182397 A1 | 7/2015 | Palashewski et al. |
| 2015/0182399 A1 | 7/2015 | Rose et al. |
| 2015/0182418 A1 | 7/2015 | Zaiss |
| 2015/0290059 A1 | 10/2015 | Brosnan et al. |
| 2015/0351982 A1* | 12/2015 | Krenik ................ A47C 23/06 5/616 |
| 2016/0015184 A1 | 1/2016 | Nunn et al. |
| 2016/0058641 A1 | 3/2016 | Moutafis et al. |
| 2016/0073789 A1* | 3/2016 | Hyltenfeldt .......... A47C 27/061 5/720 |
| 2016/0100696 A1 | 4/2016 | Palashewski et al. |
| 2016/0192886 A1 | 7/2016 | Nunn et al. |
| 2016/0242562 A1 | 8/2016 | Karschnik et al. |
| 2016/0367039 A1 | 12/2016 | Young et al. |
| 2017/0000685 A1 | 1/2017 | Rohr et al. |
| 2017/0003666 A1 | 1/2017 | Nunn et al. |
| 2017/0035212 A1 | 2/2017 | Erko et al. |
| 2017/0049243 A1 | 2/2017 | Nunn et al. |
| 2017/0065220 A1 | 3/2017 | Young et al. |
| 2017/0128297 A1 | 5/2017 | Cernasov et al. |
| 2017/0173262 A1 | 6/2017 | Veltz |
| 2017/0191516 A1 | 7/2017 | Griffith et al. |
| 2017/0208941 A1 | 7/2017 | Trakic |
| 2017/0224124 A1 | 8/2017 | Blumberg |
| 2017/0303697 A1 | 10/2017 | Chen et al. |
| 2017/0312155 A1 | 11/2017 | Copetti |
| 2017/0354268 A1 | 12/2017 | Brosnan et al. |
| 2017/0356815 A1 | 12/2017 | Madden et al. |
| 2018/0036198 A1 | 2/2018 | Mergl |
| 2018/0192781 A1* | 7/2018 | Hyltenfeldt ........ A47C 23/0435 |
| 2018/0199726 A1* | 7/2018 | Greenhalgh ......... A47C 31/123 |
| 2019/0133331 A1 | 5/2019 | Kramer |
| 2020/0187664 A1 | 6/2020 | Duncan |
| 2020/0187665 A1 | 6/2020 | Duncan |
| 2021/0307529 A1 | 10/2021 | Ki |

FOREIGN PATENT DOCUMENTS

| | | |
|---|---|---|
| CA | 1281820 C | 3/1991 |
| CA | 77379 S | 10/1995 |
| CN | 204306471 U | 5/2015 |
| EP | 2893847 A1 | 7/2015 |
| EP | 3034060 A1 | 6/2016 |
| NL | 1035506 C2 | 12/2009 |
| WO | 0002516 A1 | 1/2000 |
| WO | 2007070397 A2 | 6/2007 |
| WO | 2016138082 A1 | 9/2016 |

OTHER PUBLICATIONS

International Searching Authority, Search Report and Written Opinion for related PCT/US2019/066348, dated Feb. 21, 2020; 10 pages.

International Searching Authority, Search Report and Written Opinion for related PCT/US2019/066362, dated Feb. 20, 2020; 8 pages.

Excel Medical Supplies, "Alternating Pressure and Continuous Low Air Loss Relief", Published Apr. 1, 2014; Retrieved from Internet on May 26, 2016; 1 page.

Muscular Dystrophy Association, "One Good Turn", Published Aug. 31, 2006; <https://www.mda.org/quest/article/one-good-turn>, Retrieved from the Internet on Dec. 13, 2019; 10 pages.

Smart Mattress Company BV, "Smart Mattress"; <http://www.smartmattress.nl/?lang=en>, Retrieved from the Internet on Dec. 13, 2019; 1 page.

International Searching Authority, Search Report and Written Opinion for related PCT/US2019/066368, dated Apr. 2, 2020; 10 pages.

\* cited by examiner

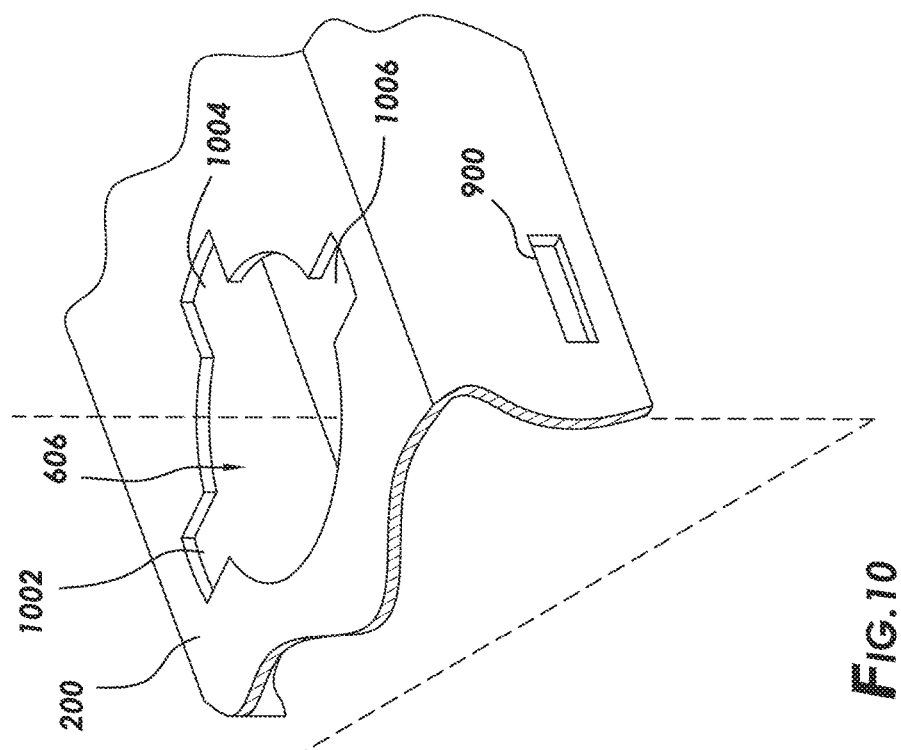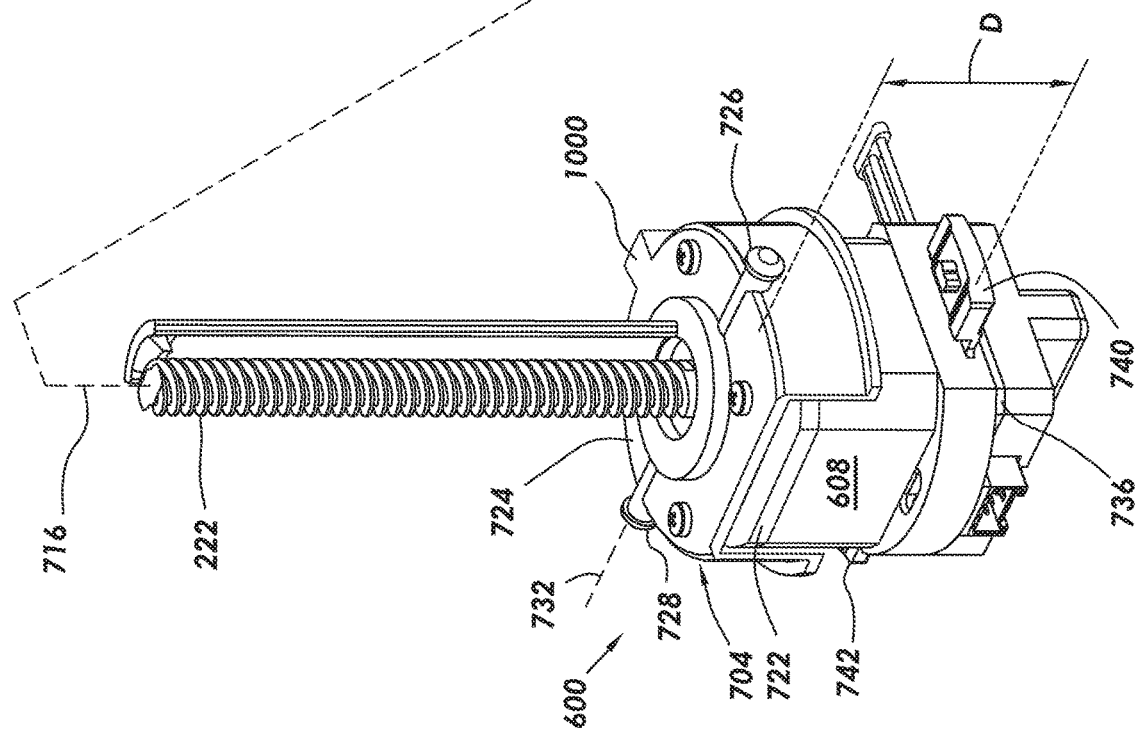
FIG.10

METHODS AND SYSTEMS OF SPRING MODULES FOR AN ADJUSTABLE SLEEPING SYSTEM

CROSS-REFERENCE TO RELATED APPLICATIONS

This application claims the benefit of provisional application Ser. No. 62/779,629, filed Dec. 14, 2018, titled "Adjustable Sleeping System", and the provisional application is incorporated by reference herein as if reproduced in full below.

BACKGROUND

Getting a good night's sleep is important, not only from the perspective of day-to-day cognitive functions, but also from the perspective of long term health. Some studies suggest that lack of sleep, or lack of sufficiently restful sleep, has long term health consequences. The long term health consequences include increased risk of dementia and Alzheimer's disease. Some factors that adversely affect the ability to get a good night's sleep are physiological, such as snoring, central apnea, obstructive apnea, and restless leg syndrome. However, other factors are environmental, such as the compliance of the sleeping surface upon which sleep is attempted, and sleeping position (though some physiological factors are sleep position dependent).

Many mattresses and beds purport to increase the restfulness of sleep. For example, one attempt in recent years is based on mattresses made of combinations of closed- and open-cell foams that purport to reduce high force areas regardless of sleep position, and to reduce communication of movement to sleeping partners. Other attempts in recent years use air bladders to create individual pockets of support, usually in horizontal rows across the width of a mattress. The air bladder mattresses enable changing air pressure within the bladders, and thus changing the force carried by each bladder. Each system has its respective drawbacks.

Any system and/or method which increases user comfort and flexibility of control would provide a competitive advantage in the marketplace.

BRIEF DESCRIPTION OF THE DRAWINGS

For a detailed description of example embodiments, reference will now be made to the accompanying drawings in which:

FIG. 10 shows a partial perspective, partial cut-away, view of an adjustable spring assembly and spring rail in accordance with at least some embodiments;

DEFINITIONS

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

The adjustable spring assemblies are described herein to have multiple rotational orientations relative to the spring rail (and the rotational orientations about a longitudinal central axis of a lead screw). However, having a first rotational orientation and a second rotational orientation shall not be read to require that the rotational orientations be simultaneously present.

" Controller" shall mean, alone or in combination, individual circuit components, an application specific integrated circuit (ASIC), a microcontroller (with controlling software), and/or a processor (with controlling software), configured to read signals and take control actions responsive to such signals.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various embodiments are directed to adjustable sleeping systems. More particular, example embodiments are directed to an adjustable sleeping system comprising a plurality of spring modules coupled to an underlying bed frame. Each spring module may comprise a plurality of adjustable spring assemblies, and the weight or force carried by each adjustable spring assembly may be changed to accomplish any of a variety of firmness settings or functions.

The specification first turns to a high level overview of the adjustable sleeping system in accordance with example embodiments.

Figure 1:
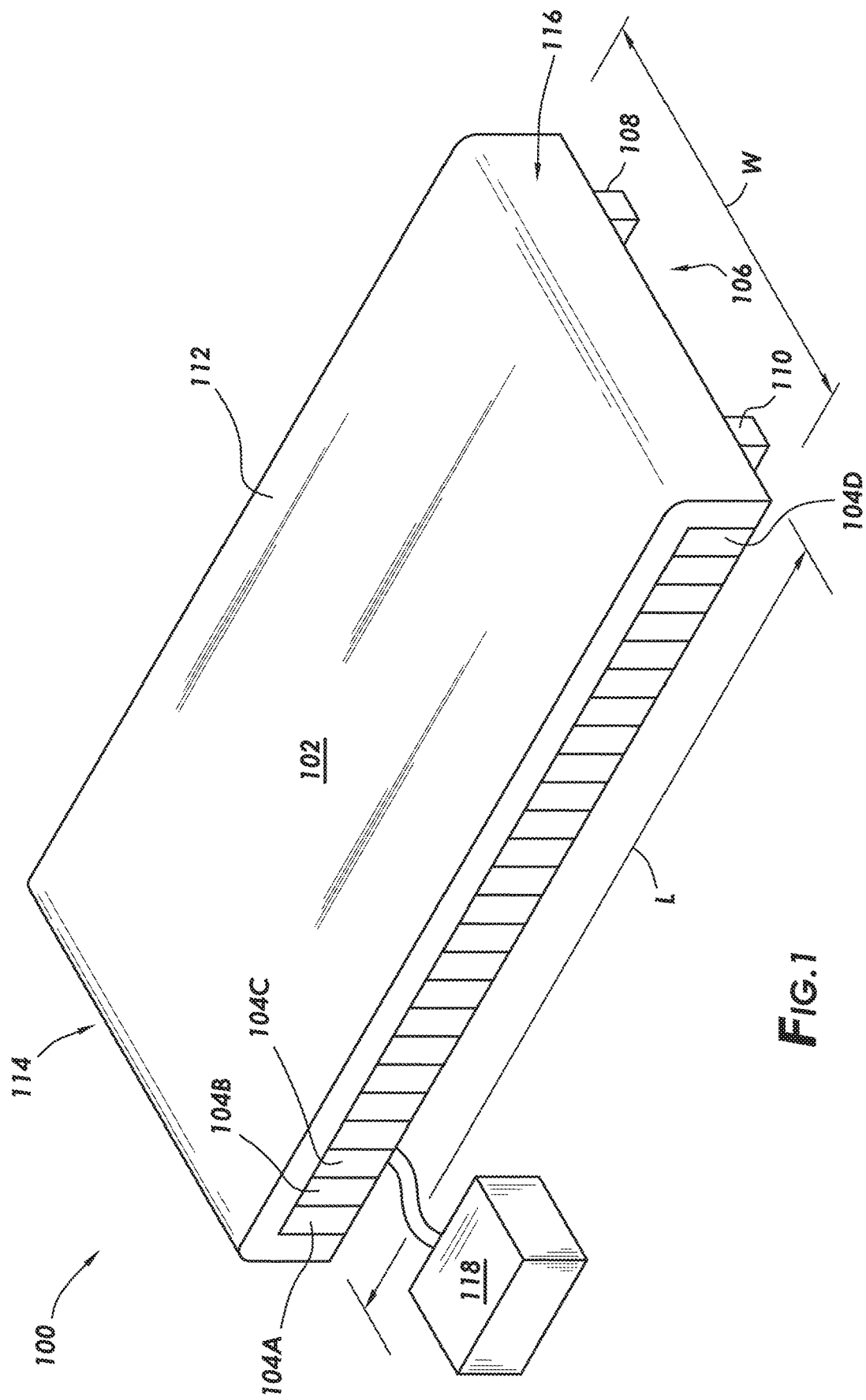
FIG. 1 shows a perspective view of an adjustable sleeping system in accordance with at least some embodiments.

FIG. 1 shows a perspective view of an adjustable sleeping system 100 in accordance with at least some embodiments. In particular, the example adjustable sleeping system 100 defines a length L, a width W, and a sleeping surface 102. The length L and width W may be any suitable size, such as a cot size, a single size, a twin size, a twin XL size, a full size, a Queen size, a "California" King, King size, or specialty sizes (e.g., for boats, motor homes, travel trailers). In some cases, the overall bed may comprise two adjustable sleeping systems 100 arranged side-by-side (e.g., two twin XL size beds side-by-side to form a King size). The adjustable sleeping system 100 further comprises a plurality of spring modules 104. In some cases, between 15 and 80 spring modules 104 may be used, in one example case between 20 and 30 spring modules 104 may be used, and in some cases 25 spring modules are used. FIG. 1 labels only four of the spring modules 104 (104A-104D) so as not to unduly complicate the figure. The spring modules are modular components that may be placed at any location, and thus a single spring module will be referred to as "spring module 104" and groups of spring modules will be referred to as "spring modules 104". The spring modules 104 mechanically coupled to a bed frame 106 comprising a first frame rail 108 and a second frame rail 110.

In the example system, an upper surface of the spring modules 104 (the upper surface not visible in FIG. 1) is covered with a topper or overlay 112, such as open-cell or closed-cell foam. In one example embodiment the overlay 112 comprises a foam padding having a thickness of three inches (measured perpendicularly to the sleeping surface 102). Other thicknesses, both greater and smaller, and other constituent materials, may be used. In the example of FIG. 1, the overlay 112 wraps around the head end 114 of the adjustable sleeping system 100, and also wraps around the foot end 116 of the adjustable sleeping system 100. In other cases, the wrapping aspects of the overlay 112 may be omitted, and a spring module 104 on the head end 114 will be exposed on the head end 114, and another spring module 104 will be exposed on the foot end 116. In yet still other cases, the overlay 112 may be omitted entirely, and thus an upper surface defined by the spring modules 104 may define the sleeping surface 102.

Still referring to FIG. 1, the spring modules 104 can be considered to be arranged in a column along the length L, with each spring module 104 defining a row within the column. Each spring module 104 is coupled to the first frame rail 108 of the bed frame 106, and each spring module 104 is coupled to the second frame rail 110 of the bed frame 106.

The adjustable sleeping system 100 further comprises a bed controller 118 communicatively and controllably coupled to each spring module 104, and as discussed more below communicatively and controllably coupled to the adjustable spring assemblies (not visible in FIG. 1) within each spring module 104. The bed controller 118 is configured to selectively control a load carried by each spring module 104, and more particularly to selectively control a load carried by each adjustable spring assembly within each spring module 104. The bed controller 118 may take any suitable form, such as a computer system, individual circuit components, an application specific integrated circuit (ASIC), a microcontroller (with controlling software), a processor (with controlling software), or combinations thereof configured to read signals and take control actions responsive to such signals.

Figure 2:
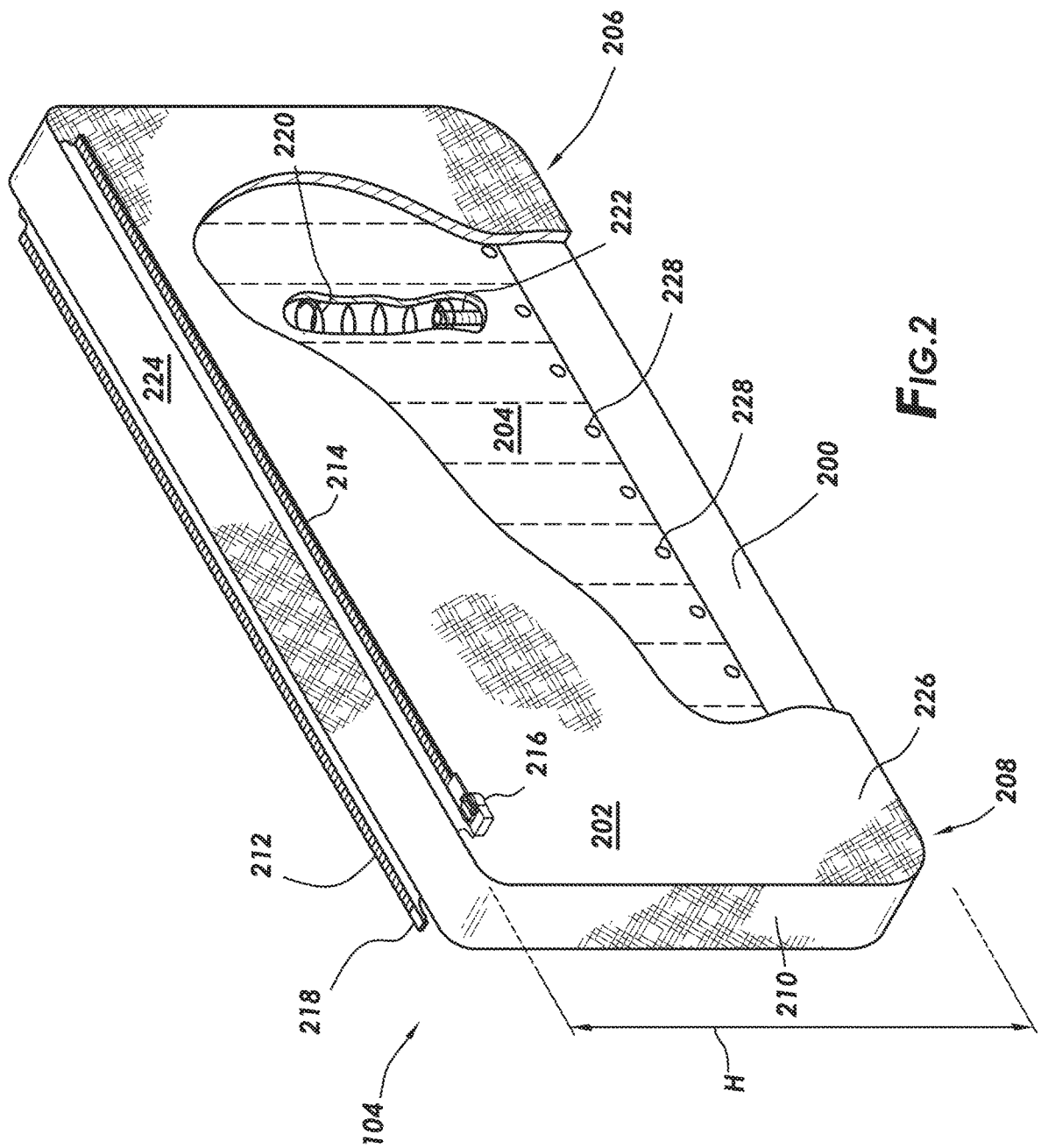
FIG. 2 shows a perspective view of a spring module in accordance with at least some embodiments.

FIG. 2 shows a perspective, partial cut-away, view of a spring module 104 in accordance with at least some embodiments. In particular, FIG. 2 shows a spring rail 200, a slip cover 202, and a baffle box 204. The spring rail 200 in accordance with example embodiment is a metal rail that forms the base of the spring module 104. In some cases the spring rail 200 has a cross-sectional shape in the form of an inverted channel shape, with the walls or legs of the channel pointing downward (i.e., downward referenced to the force of gravity), and having a flat upper surface. The spring rail 200 is discussed in greater detail below.

The example slip cover 202 is a cover of fabric material. The slip cover 202 wraps around a bottom of the spring rail 200 on opposing ends 206 and 208 of the spring rail 200. When assembled into an adjustable sleeping system, either or both of the ends 206 and 208 may be the location where a fitted sheet wraps around the overall adjustable sleeping system. In example systems, the slip cover 202 does not fully envelope the spring rail 200, as the spring rail 200 couples to an underlying bed frame 106 (FIG. 1), and the spring rail 200 is thus exposed on a lower side. When assembled into an adjustable sleeping system, one or both of the short sides of the spring module 104 may be visible along the length L (FIG. 1) of the adjustable sleeping system. For example, when assembled the short side 210 may be visible along the length L of the adjustable sleeping system. If the spring modules 104 are part of the twin-size bed, the opposite short side (not visible in FIG. 2) would also be exposed and visible. On the other hand, if the spring modules 104 are part of a Queen- or King-size bed, only one of the short sides may be visible as another twin-size set of spring modules 104 will block exposure of the second side. Because of the visibility of the short sides (e.g., short side 210), the slip cover 202 material may be selected to accomplish an overall industrial design and/or marketing feature. Thus, the example slip cover 202 covers the short side 210, the opposite short side not visible in FIG. 2, the top 224, the long side 226, the opposite long side not visible in FIG. 2, and portions of the spring rail 200.

In order to assemble the adjustable sleeping system, a plurality of spring modules 104 are coupled side-by-side (e.g., as shown in FIG. 1). To keep objects from slipping down between spring modules 104, and/or to form a stable upper surface that may be the sleeping surface (or that may be parallel to the sleeping surface 102), the example slip cover 202 also defines affixation devices 212 and 214 across an upper portion of the slip cover 202. The affixation devices 212 and 214 are disposed along the long dimension of the spring module 104. In some cases, and as shown, the affixation devices 212 and 214 are elements of a zipper. For example, affixation device 214 may include a slider 216 and a plurality of teeth. Thus, the affixation device 214 is configured to couple to a complementary affixation device on an adjacent spring module. The affixation device 212 may include a pin 218 and a plurality of teeth. Thus, the affixation device 212 is configured to couple to a complementary affixation device on an adjacent spring module. However, the affixation devices 212 and 214 may take any suitable form, such as a series of buttons and corresponding series of button holes, or eyelets through which laces are weaved. In the example embodiments of FIG. 2, the affixation devices 212 and 214 are shown at the upper portion of the spring module 104, and particularly along seams of the slip cover 202 at the intersection of the top 224 and long side 226 of the spring module 104; however, in other cases the affixation devices 212 and 214 need not be precisely at the upper corners, and may be disposed lower. In particular, the spring module 104 may define a height H (e.g., between 10 and 20 inches, in some cases between 12 and 18 inches), and the affixation devices may run along the long dimension at a distance half the height H or less from the intersection of the top 224 and long side 226, and in some cases a quarter of the height H or less from the from the intersection of the top 224 and long side 226.

The example slip cover 202 is shown in partial cut-away to expose the underlying baffle box 204 of fabric coupled to the spring rail 200. As will be discussed in greater detail below, the baffle box 204 covers and separates the upper components of adjustable spring assemblies (not visible in FIG. 2) of the spring module 104. The dashed lines associated with the baffle box 204 show locations of baffles within the baffle box 204, and main springs and other components of the adjustable spring assemblies extend upward into pockets formed by the baffles within the baffle box 204. The baffle box 204 is likewise shown in partial cut-away to show an example main spring 220 and lead screw 222 of an adjustable spring assembly. The baffle box 204 and adjustable spring assemblies (e.g., one adjustable spring assembly associated with main spring 220 and lead screw 222) are discussed in greater detail below. Nevertheless, the baffle box 204, and thus the pockets formed within the baffle box 204, are coupled on a lower end to the spring rail 200, such as by affixation devices 228. As discussed more below, in some cases the baffle box 204 is coupled in such a way that tension created in the main springs (e.g., main spring 220) by the baffle box 204 is not transmitted directly to the spring rail 200, so as not to pre-load force sensors associated with the adjustable spring assemblies (the coupling discussed more below).

Returning to FIG. 1, assembly of an adjustable sleeping system in accordance with various embodiments may involve coupling a first spring module (e.g., spring module 104A) to the bed frame 106. Next, the method may comprise coupling a second spring module (e.g., spring module 104B) to the bed frame 106. The process of coupling spring modules continues (e.g., with spring module 104C) until the last spring module (e.g., spring module 104D) has been coupled to the bed frame 106. In some cases, just after a spring module 104 is coupled to the bed frame 106, the upper edge of the spring module is coupled to the upper edge of the adjacent spring module (e.g., using affixation devices 212 and 214 discussed above). In other cases, the assembly may wait until some or all the spring modules 104 are coupled to the bed frame before coupling the affixation devices to secure upper ends of the spring modules 104. Once assembled, the upper surfaces of the spring modules 104 define a surface parallel to a sleeping surface of the adjustable sleeping system 100 of FIG. 1. In cases where the overlay 112 is omitted, the upper surfaces 224 (FIG. 2) of the spring modules 104 may directly form sleeping surface.

Figure 3:
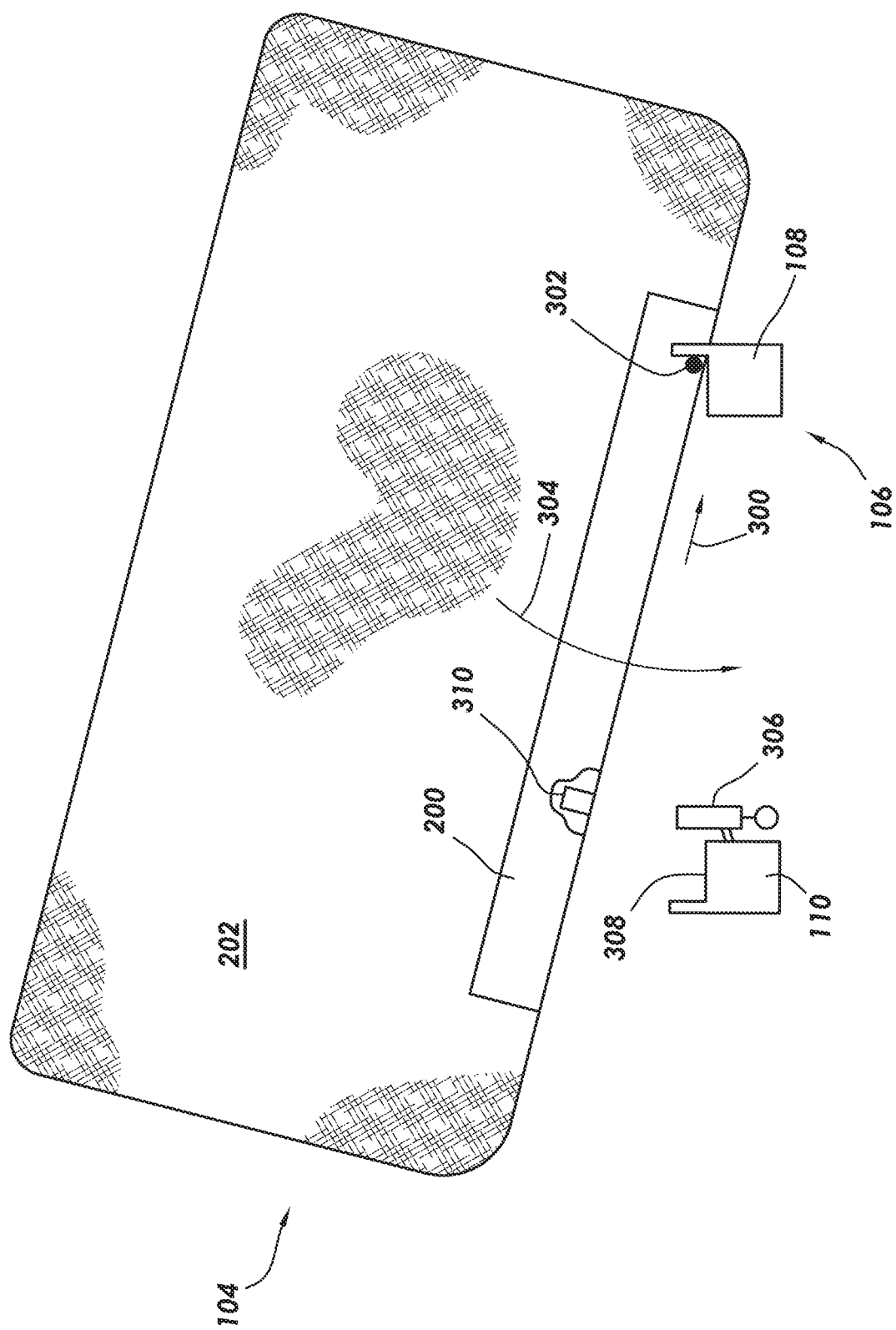
FIG. 3 shows a side elevation view of a spring module and bed frame during installation of the spring module, and in accordance with at least some embodiments.

FIG. 3 shows a side elevation view of a spring module 104 and bed frame 106 during installation of the spring module 104, and in accordance with at least some embodiments. Visible in FIG. 3 are the spring module 104, the first frame rail 108, and the second frame rail 110 (where the frame rails 108 and 110 are part of the bed frame 106). The spring module 104 of FIG. 3 includes the slip cover 202, and the exposed portion of the spring rail 200. In example embodiments, coupling each spring module 104 to the bed frame 106 is a two-step process. First, the spring module 104 is coupled to the first frame rail 108. Though not visible in FIG. 3, the first frame rail 108 extends along and parallel to the length L (FIG. 1, and where the length L is into and out of the page in the view of FIG. 3). The second frame rail 110 also runs along and parallel to the length L (again, into and out of the page in the view of FIG. 3).

FIG. 3 shows a first step in the example process of coupling the spring module 104 to the underlying bed frame 106, where the spring module 104 is in operational relationship to the first frame rail 108 but not in contact with the second frame rail 110. In example cases, the spring module 104 is placed on the first frame rail 108, and then the spring module 104 is slid across the first frame rail 108 until a first hinge member of the spring module 104 couples to a second hinge member of the first frame rail 108. The direction of the sliding is shown by arrow 300. More particularly still, the spring rail 200 is placed in direct contact with the frame rail 108 at an angle such that the spring module 104 initially only contacts the first frame rail 108. The spring module 104 is then slid in a direction indicated by arrow 300 until the first and second hinge members couple together. In other cases, the sliding may be omitted, and the spring module 104 may be directly placed against the frame rail 108 in such a way that the hinge members couple together. Any suitable hinge member on the spring module 104, and any complementary hinge member on the first frame rail 108, may be used. Example hinge members are discussed below. Nevertheless, when coupled the first and second hinge members define a rotational axis, such as rotational axis 302 parallel to the first frame rail 108. In the view of FIG. 3, the rotational axis 302 is perpendicular to the plane of the page, and thus the rotational axis 302 is shown as a point. Coupling the spring module 104 may then further comprise rotating the spring module 104 about the rotational axis 302, with the rotation shown by curved arrow 304. The rotation of the spring module 104 moves the elevated portion of spring module 104 toward the second frame rail 110, and the spring module 104 then latches to the second frame rail 110 (the latched spring module not shown in FIG. 3, but is shown FIG. 1). The process is repeated for each spring module 104 (e.g., spring module 104A, spring module 104B, spring module 104C, and spring module 104D) in the adjustable sleeping system.

In at least some cases, the rotation and latching of the spring module 104 also acts to electrically couple an electrical connector of the spring module 104 to an electrical connector associated with the second frame rail 110. Electrically coupling the connectors communicatively couples the spring module 104 to the bed controller 118 (FIG. 1). More particularly, electrically coupling the connectors communicatively couples the adjustable spring assemblies (discussed more below), which make up the spring module 104, to the bed controller 118. FIG. 3 shows an electrical connector 306 rigidly coupled on an inside surface of the second frame rail 110. That is, in the example of FIG. 3 the surface to which the electrical connector 306 is coupled is a surface that faces the first frame rail 108. The electrical connector 306 extends upward above a seating surface 308 such that, when the spring module 104 is coupled to the second frame rail 110, the electrical connector extends upward in a channel defined by spring rail 200. FIG. 3 also shows, in a partial cutaway, a corresponding electrical connector 310 within the channel defined by the spring rail 200. Thus, in some cases the act of rotating the spring module 104 about the rotational axis 302 not only results in latching of the spring module 104 to the second frame rail 110, but also mechanically and electrically couples the electrical connector 310 of the spring module 104 to the electrical connector 306 attached to the second frame rail 110. Any suitable electrical connectors may be used. In alternative embodiments, the electrical connector 306 may be partially disposed within an interior volume of the second frame rail 110, with the electrical connector 306 extending above the seating surface, and thus power and communication conductors may extend along an interior volume of the second frame rail. In yet still other cases, coupling the electrical connectors may be disassociated from latching of the spring module to the second frame rail 110. For example, coupling the electrical connectors may be a separate step, or the electrical connectors may be associated with the location of the first frame rail 108 such that sliding the spring module 104 across the first frame rail 108 results in mechanically and electrically coupling the connectors.

Figure 4:
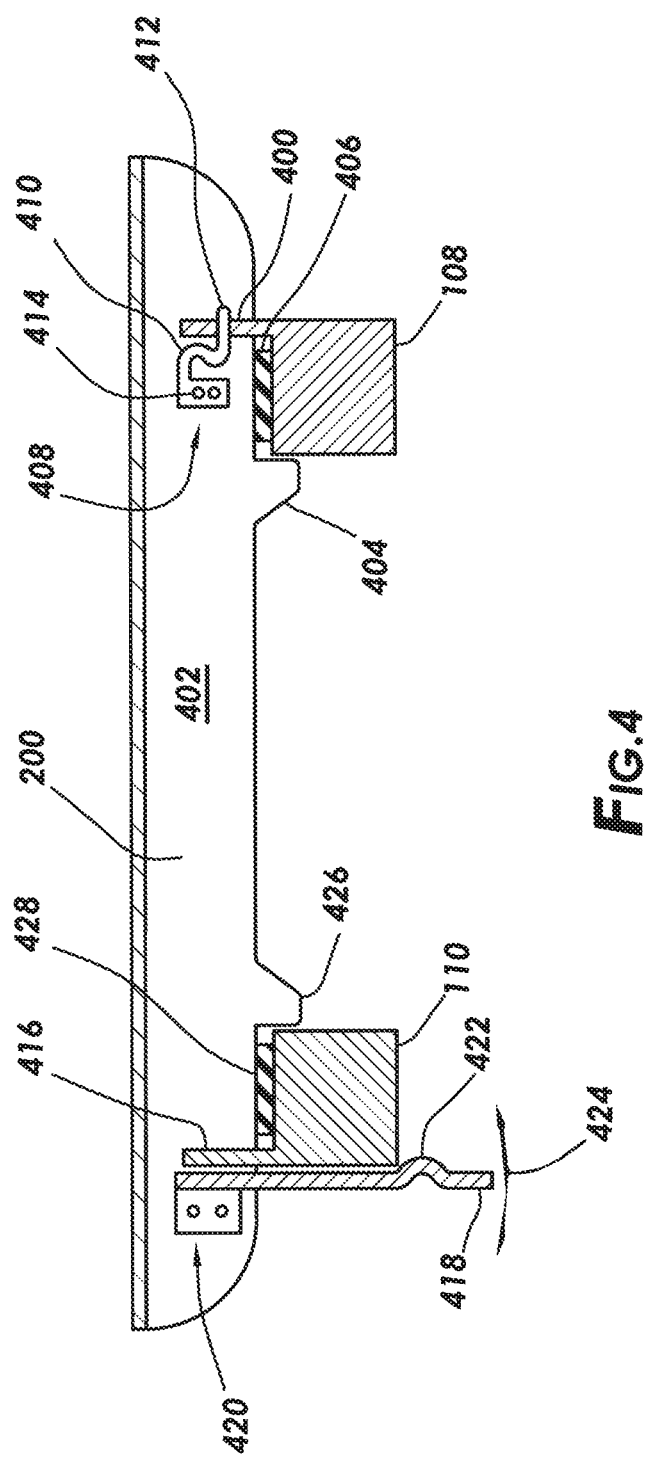
FIG. 4 shows a cross-sectional view of spring rail coupled to an underlying first and second frame rails, in accordance with at least some embodiments.

FIG. 4 shows a cross-sectional view of spring rail coupled to an underlying first and second frame rails, in accordance with at least some embodiments. In particular, visible in FIG. 4 are the first frame rail 108, the second frame rail 110, and the spring rail 200. The spring rail 200 is shown without the slip cover, without the baffle cover, and without the adjustable spring assemblies, all so as not to further complicate the figure. The first frame rail 108 and second frame rail 110 are show as solid objects, but in other cases the frame rails may be hollow (e.g., tubing with a square or rectangular cross- section). The first frame rail 108 defines an upwardly projecting wall 400 that extends parallel to the length L (FIG. 1). In the view of FIG. 4, the upwardly projecting wall extends into and out of the plane of the page. Though the upwardly projecting wall 400 is shown on the outer edge of the first frame rail 108 (e.g., outer relative to location of the second frame rail 110), the upwardly projecting wall 400 may be at any suitable location (e.g., inner edge, middle). At the location of each spring module, the example upwardly projecting wall 400 has two slots, one slot for each downwardly projecting wall or downwardly projecting leg of a spring rail 200 (e.g., downwardly projecting 402). The slots are not visible in FIG. 4, and only one downwardly projecting leg visible in the cross-section of FIG. 4. Nevertheless, as part of coupling the spring module 104 to the first frame rail 108, each downwardly projecting leg of the spring rail 200 is placed within a corresponding slot defined in the upwardly projecting wall 400.

In the example embodiment shown in FIG. 4, the spring rail 200 shows two example hinge members associated with the first frame rail 108, but it is to be understood that the two example hinge members need not be simultaneously present. The first example hinge member is a tab 404 projecting downward below the bottom edge of the downwardly projecting leg 402. In some cases, both the downwardly projecting legs of the spring rail 200 will have a corresponding tab. When the spring rail 200 is placed on and slid across the first frame rail 108 as part of the installation, the tab 404 acts as a stop to orient the spring rail 200 relative to the first frame rail 108. The tab 404 further holds a the downwardly projecting leg 604, and thus the spring module 104, in proper orientation as the spring rail 200 is rotated to contact the second frame rail 110. In some cases, one or both of the downwardly projecting legs (e.g., downwardly projecting leg 402) has an inwardly projecting tab, and as the opposite end of the spring rail 200 latches to the second frame rail 110, the inwardly projecting tab engages a complementary feature in the upwardly projecting wall 400. The engagement of the inwardly projecting tab biases the spring rail 200 toward the first frame rail 108. In some cases, and as shown, the zone between the bottom edge of downwardly projecting leg 402 and the contact surface of the first frame rail 108 includes a polymeric material 406. The polymeric material 406 may provide an opposing force to the bias toward the first frame rail 108 provided by the spring rail 200, and may also reduce the conduction of vibrations from the spring module to the underlying first frame rail 108.

The second example hinge member visible in FIG. 4 is a reverse-"S" shaped spring clip 408 (hereafter referred to as "tusk 408" given the resemblance to a tusk of an elephant). The example tusk 408 defines a stop portion 410 being a rounded upper portion, a tusk portion 412, and a connection portion 414. The stop portion 410 and tusk portion are free to move in a plane parallel to a plane defined by the inwardly facing surface of the downwardly projecting leg 402, while the connection portion 414 is rigidly coupled to the downwardly projecting leg 402. In these example embodiments, when the spring rail 200 is placed on and slid across the first frame rail 108 as part of the installation, the stop portion 410 abuts a portion of the upwardly projecting wall 400 and thus acts as a stop to orient the spring rail 200 relative to the first frame rail 108. In addition to, or in place of, the stop portion 410 abutting the upwardly projecting wall 400, the tab 404 may provide the functionality. As the spring rail 200 is rotated downward to contact the second frame rail 110, the tusk portion 412 engages a complementary feature in the upwardly projecting wall 400. The engagement of the tusk portion 412 (because of the spring action of the tusk 408) and a corresponding hinge member in the form of the upwardly projecting wall 400, biases the spring rail 200 toward the first frame rail 108. And again in the embodiments using the tusk 408, the zone between the bottom edge of downwardly projecting leg 402 and the contact surface of the first frame rail 108 may include the polymeric material 406.

Still referring to FIG. 4, and particularly referring to the interaction of the spring rail 200 with the second frame rail 110. The second frame rail 110 also defines an upwardly projecting wall 416 that extends parallel to the length L (FIG. 1) of the adjustable sleeping system. In the view of FIG. 4, the upwardly projecting wall 416 extends into and out of the plane of the page. Though the upwardly projecting wall 416 is shown on the outer edge of the second frame rail 110 (e.g., outer relative to location of the first frame rail 108), the upwardly projecting wall 416 may be at any suitable location (e.g., inner edge, middle). At the location of each spring module, the upwardly projecting wall 416 has two slots, one slot for each downwardly projecting leg of a spring rail 200. The slots are not visible in FIG. 4, and only one downwardly projecting leg 402 of the spring rail 200 is shown in the cross-sectional view of FIG. 4. Nevertheless, as part of coupling the spring module 104 to the second frame rail 110, each downwardly projecting leg 402 of the spring rail 200 is placed within a corresponding slot defined in the upwardly projecting wall 416. The slots within the upwardly projecting wall 416 are considered latching members, as the slots hold the spring rail 200 in the proper location along the second frame rail 110.

In the example embodiment shown in FIG. 4, the spring rail 200 has an example latch member in the form of spring latch 418. In particular, the example spring latch 418 (shown in partial cross-sectional form) defines a proximal portion 420 rigidly coupled to the spring rail 200, and more particularly rigidly coupled to the downwardly projecting leg 402. In some cases, the spring latch 418 is rigidly coupled on its proximal end 420 to both downwardly projecting legs of the spring rail 200. As the spring module is rotated toward the second frame rail 110 during installation, the spring latch 418 is initially deflected by an outer edge of the spring rail 200. In particular, the interaction of an inwardly protruding ridge 422 (hereafter just ridge 422) causes deflection of the spring latch 418 as the ridge moves across the second frame rail 110. Once the ridge 422 clears the lower boundary of the second frame rail 110, the spring action of the spring latch 418 causes the ridge 422 to couple beneath the second frame rail 110. The movement of the spring latch 418 is shown by double-headed arrow 424. In some cases, the spring latch 418 may be sufficient to couple or latch the spring rail 200 the second frame rail 110, but in other cases each downwardly projecting leg of the spring rail 200 (e.g., downwardly projecting leg 402) may further include a tab 426 to help ensure that the spring latch 418 is properly aligned. Depending on the shape of the ridge 422, the spring latch 418 may provide a force that biases the spring rail 200 toward the second frame rail 110 when in the latched orientation.

In some example cases, the zone between the bottom edge of downwardly projecting leg 402 and the contact surface of the second frame rail 110 includes a polymeric material 428. The polymeric material 428 may provide an opposing force to the bias toward the second frame rail 110 provided by the spring latch 418, and may also reduce the conduction of vibrations from the spring module to the underlying second frame rail 110.

Figure 5:
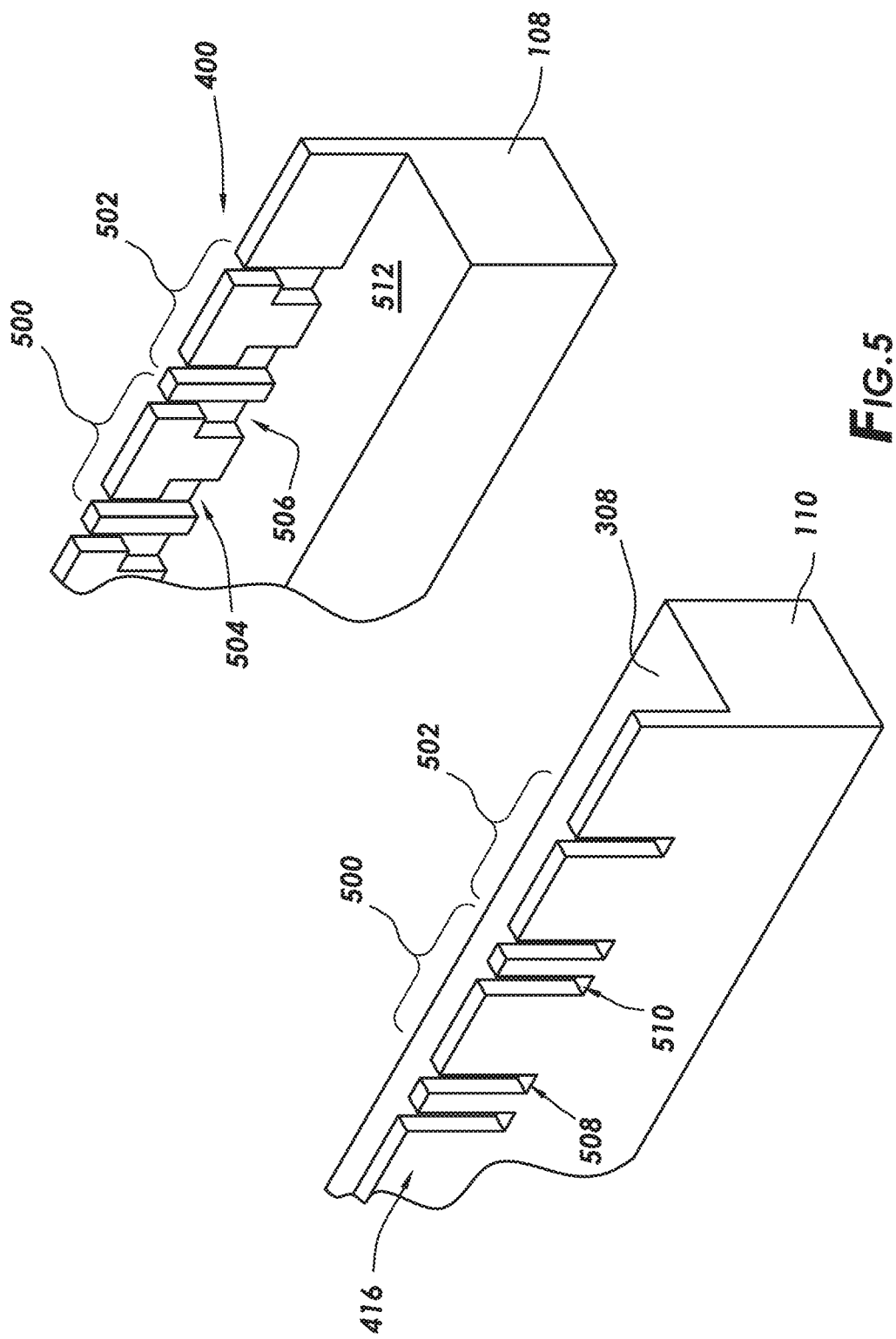
FIG. 5 shows a partial perspective view of the frame rails of the bed frame in accordance with at least some embodiments.

FIG. 5 shows a partial perspective view of the frame rails of the bed frame in accordance with at least some embodiments. In particular, FIG. 5 shows a portion of the first frame rail 108 and the second frame rail 110. Visible in FIG. 5 are a portion of the upwardly projecting wall 400 of the first frame rail 108, as well as a portion of the upwardly projecting wall 416 of the second frame rail 110. The example upwardly projecting wall 400 defines two zones where respective spring modules may couple, the zones being zone 500 and zone 502. The example upwardly projecting wall 416 also defines two zones where spring modules may couple, and those zones are also designated as zones 500 and 502 to show the correspondence of the locations with respect to the first frame rail 108. Thus, a spring module coupled to the first and second frame rails 108 and 110 will couple within a zone. FIG. 5 shows two complete zones 500 and 502, as well as a partial zone to the left on each frame rail. Only two zones are shown so as to provide sufficient detail of the hinge and latch members in those zones, and also to acknowledge that in at least some embodiments the frame rails 108 and 110 may be contiguous over less than all the spring modules that make up an adjustable sleeping system (e.g., system that implement separate inclination of the head, torso, and legs).

Referring initially to the first frame rail 108, and specifically zone 500, as illustrative of any zone along the first frame rail 108. The upwardly projecting wall 400 defines two slots 504 and 506. The slots 504 and 506 extend from the upper surface of the upwardly projecting wall 400 to the seating surface 512. In the example case of FIG. 5, the slot 504 is an "L"-shaped slot, and slot 506 is a mirror image across the zone such that the center piece between the slots forms a "T" shape. In embodiments using the tusk 408 (FIG. 4), the wider portion of the "T" shape is the location where the stop portion 410 (FIG. 4) of the tusk 408 abuts upwardly projecting wall 400 to control the position of the spring rail in its movement across the first frame rail 108 during installation. The interior shoulder region formed by the "T" shape on each side (in this case, the shoulder created by an absence of material) is a surface that enables application of the biasing force. In the example embodiments using the tusk 408, the tusk portion 412 interacts with the shoulder region created by one side of the "T" shape to provide the biasing force. If two tusks 408 are used on a single spring rail, each tusk will provide a portion of the biasing force. Regardless, the slots 504 and 506 are illustrative of hinge members defined on the first frame rail 108.

Referring now to the second frame rail 110, and specifically zone 500, as illustrative of any zone along the second frame rail 110. The upwardly projecting wall 416 defines two slots 508 and 510. The slots 508 and 510 extend from the upper surface of the upwardly projecting wall 416 to the seating surface 308. The example slots 508 and 510 have a uniform width along their length, and the example slots 508 and 510 act to guide the downwardly projecting legs of a spring rail (e.g., downwardly projecting leg 402 of spring rail 200 of FIG. 4) into contact with the seating surface 308. The slots 508 and 510, along with the outside surface of the second frame rail 110 across which ridge 422 slides, are alone or in combination illustrative of latch members defined on the second frame rail 110. The specification now turns to a more detailed discussion of the example spring modules 104.

Figure 6:
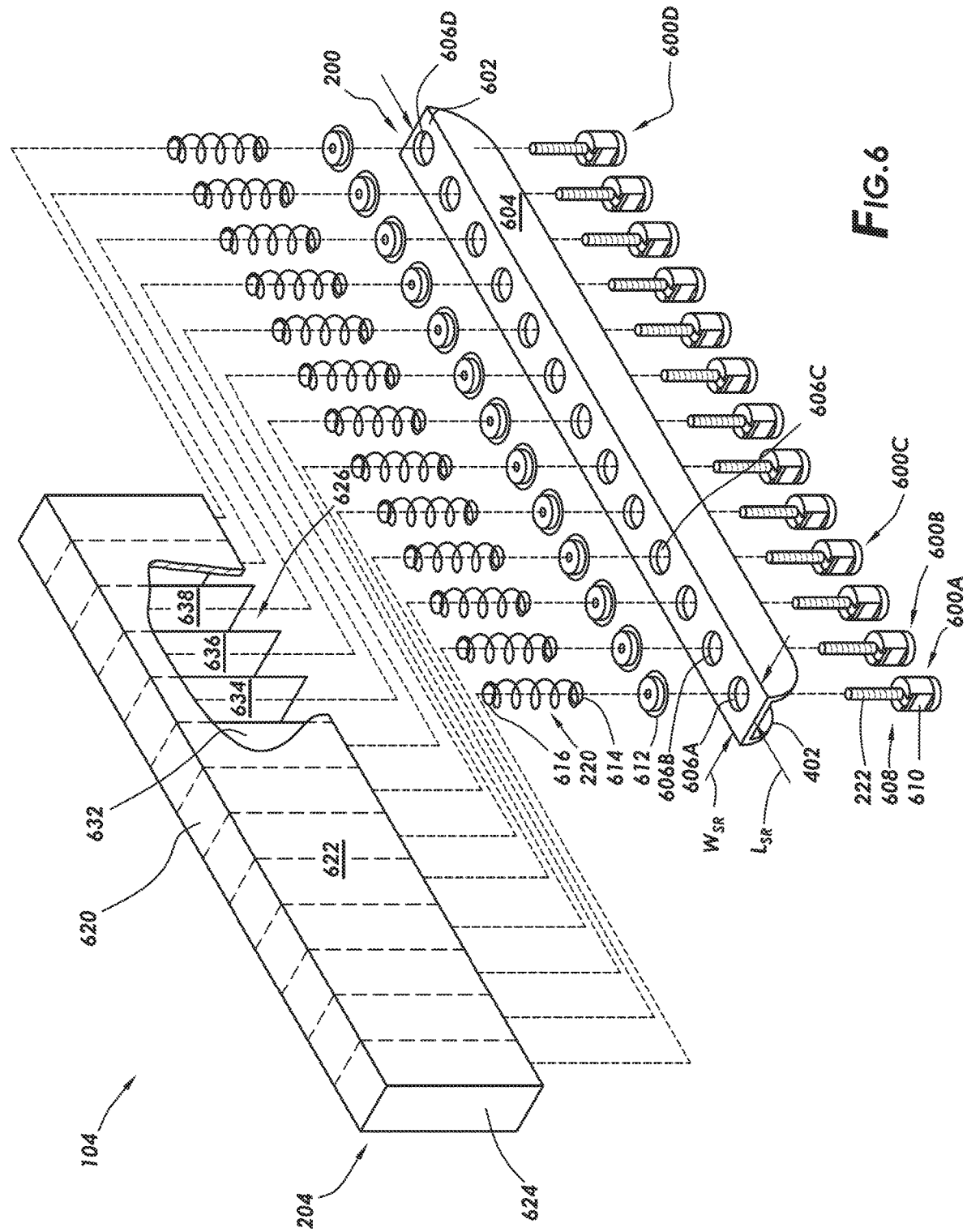
FIG. 6 shows an exploded perspective view of a spring module in accordance with at least some embodiments.

FIG. 6 shows an exploded perspective view of a spring module in accordance with at least some embodiments. In particular, visible in FIG. 6 are the baffle box 204, the spring rail 200, as well as a plurality of adjustable spring assemblies 600. In some cases, between 8 and 40 adjustable spring assemblies 600 are used within each spring module 104, in one example case between 10 and 15 adjustable spring assemblies 104, and in a particular case 13 adjustable spring assemblies 600 are used. FIG. 6 labels only four of the adjustable spring assemblies 600 (600A-600D) so as not to unduly complicate the figure. The adjustable spring assemblies are modular components that may be placed at any location within a spring module 104, and thus a single adjustable spring assembly will be referred to as "adjustable spring assembly 600" and groups of adjustable spring assemblies will be referred to as "adjustable spring assemblies 600". The slip cover 202 (FIG. 2) is not included in FIG. 6 so as not to further complicate the figure. The various example components will be addressed in turn, starting with a more detailed description of the spring rail 200.

The example spring rail 200 defines a long dimension or length $L_{SR}$. When the example spring module 104 is assembled into an adjustable sleeping system 100 (FIG. 1), the length $L_{SR}$ is parallel to the width W (FIG. 1) and perpendicular to the length L (FIG. 1) of the adjustable sleeping system 100. In cases where the adjustable sleeping system 100 is a cot width or a twin width, the length $L_{SR}$ will be about same as the width W. In cases where the overall adjustable sleeping system 100 is a Queen size, a "California" King, or a King size, the length $L_{SR}$ may be half the overall width W. The spring rail 200 also defines a width $W_{SR}$. When the example spring module 104 is assembled into an adjustable sleeping system 100, the width $W_{SR}$ is parallel to the length L and perpendicular to the width W of the adjustable sleeping system 100. In example cases the width $W_{SR}$ is between and including 1 inch and 6 inches, and in some cases the width $W_{SR\,is}$ 3 inches. The example spring rail 200 further comprises an upper surface 602 and a corresponding lower surface (not visible in FIG. 6). Moreover, FIG. 6 shows the example spring rail 200 to have both the downwardly projecting leg 402 on a first side of the spring rail 200 and running along the length $L_{SR}$, and a downwardly projecting wall or downwardly projecting leg 604 on the opposite side of the spring rail 200 and running along the length $L_{SR}$. Further, the example spring rail 200 defines a plurality of apertures 606. The number of apertures 606 may correspond directly to the number of adjustable spring assemblies 600, and thus in some cases between 8 and 40 apertures 600 are present within each spring module 104.

FIG. 6 labels only four of the apertures 606 (606A-606D) so as not to unduly complicate the figure. Each individual aperture 606 will be referred to as "aperture 606," and groups of apertures will be referred to as "apertures 606." The apertures 606 are spaced along the length $L_{SR}$, and each aperture 606 extends from the upper surface 602 to the lower surface of the spring rail 200. In example embodiments, the spring rail 200 is made of metallic material, but any suitable material (e.g., high strength plastic, fiber glass) may be used.

The discussion now turns to the adjustable spring assemblies 600. Referring to adjustable spring assembly 600A as representative of all the adjustable spring assemblies, the example adjustable spring assembly 600A comprises a motor 608 with a stator 610 and a rotor (the rotor not visible in FIG. 6). The rotor of the motor 608 is coupled to a lead screw 222. The motor 608 may comprise any suitable electric motor that can turn the lead screw 222, such as a stepper motor, a direct current (DC) motor, or an alternating current (AC) motor (e.g., squirrel cage or synchronous). Regardless of the type of motor 608, the motor 608 is controlled by the bed controller 118 (FIG. 1). In one example embodiment, the motor 608 is housed in a National Electrical Manufacturers Association (NEMA) 17 body, but other body types are also contemplated. In example embodiments, the stator 610 is coupled to the spring rail 200 in any suitable fashion; however, examples of how to couple the stator 610 to the spring rail 200 are discussed in greater detail below.

In the representative adjustable spring assembly 600A, the lead screw 222 is rigidly coupled to the rotor. Thus, as the rotor of the motor 608 turns, so too does the lead screw 222, but the lead screw 222 does not translate along its longitudinal axis; rather, the orientation and position of the lead screw 220 relative to the upper surface 602 remains the same. Thus, the lead screw in the example embodiments is referred to as a captive lead screw. However, in other embodiments the lead screw may be implemented as a non-captive lead screw, where turning of the rotor translates the lead screw along the longitudinal axis of the lead screw.

When assembled, the lead screw 222 extends above the upper surface 602 of the spring rail 200. A spring perch or spring plate 612 is coupled to the lead screw 222 such that as the lead screw 222 is turned by the motor 608, the spring plate 612 translates up and down along the longitudinal axis of the lead screw 222. In embodiments where the lead screw 222 is a captive lead screw, the axial relationship of the lead screw 222 to the motor 608 does not change, and the spring plate 612 is threadingly coupled to the lead screw 222 such that as the lead screw 222 turns, the axial location of the spring plate 612 along the lead screw 222 changes. In example embodiments, the lead screw 222 has an 8 millimeter diameter, but larger and smaller diameters are also contemplated.

The representative adjustable spring assembly 600A further comprises the main spring 220 in the form of a helical spring having a first end 614 and a second end 616. When assembled, the first end 614 of the main spring 220 couples to the spring plate 612, and the second end abuts an inside surface of the baffle box 204 of fabric. In example embodiments, the main spring 220 is a helical spring that is "barreled", meaning that the main spring 220 has a larger diameter at its medial portion, and smaller diameters at the first end 614 and second end 616, thus taking the exterior shape of an elongated whiskey barrel. Barreling of the main spring 220 reduces buckling of the main spring under loads tending to torque the main spring 220 across the central axis of the main spring 220. In other cases the main spring 220 may have a single diameter along the entire height. In accordance with at least some embodiments, the main spring 220 has a constant spring factor K along its length. In other cases, however, the main spring 220 may have two or more spring constants along its length. In the example case of two spring constants, a first portion having a first spring constant K1 and a second portion having a second spring constant K2, where the first spring constant K1 is different than the second spring constant K2. Having a main spring with two or more spring constants may enable finer control of the force carried for lighter loads.

Regardless of the exterior shape and/or how many spring constants the main spring 220 may implement, in example embodiments the spring has a free or un-laden height of between and including 5 inches to 20 inches, in some cases between 8 inches to 15 inches, and in a particular case about 11 inches. When the spring module 104 is fully assembled, the baffle box 204 compresses or preloads each main spring 220, making the pre-load height between and including 4 inches to 19 inches, in some cases between and including 7 inches to 14 inches, and in a particular case about 10 inches.

Still referring to FIG. 6, the example spring module 104 further comprises the baffle box 204. The example baffle box 204 is shown in partial cut-away view to highlight some of the interior components. The baffle box 204 defines a top wall 620, a first side wall 622, a second wall opposite the first side wall 622 (the second side wall not visible in FIG. 6), a first end wall 624, a second end wall opposite the first end wall 624 (the second end wall not visible in FIG. 6), and an interior volume 626. Disposed within the interior volume 626 are a plurality of baffles (e.g., baffles 632, 634, 636, 638). The locations of the remaining baffles are illustrated by dashed lines along the top wall and first side wall 622. Each baffle extends between the first side wall 622 and the second side wall, and the plurality of baffles thus create or define a plurality of pockets within the baffle box 204. When assembled, each pocket of the baffle box 204 is telescoped over a respective main spring 220 of a respective adjustable spring assembly 600. In example cases, each pocket of the baffle box 204 is coupled on a lower end directly or indirectly to the spring rail 200. In some cases, each pocket of the baffle box 204 is coupled to a top plate of the motor 600, as will be discussed in greater detail below.

The baffle box 204 in example cases is made of fabric material, and serves several purposes. First, the baffles (e.g., baffles 632, 634, 636, 638) physically separate the main springs 220 from each other to reduce or eliminate the possibility of the spring coils interfering with each other. Moreover, the baffle box 204 acts to slightly compress and thus pre-load each main spring 220. Further still, the baffle box 204 physically couples the main springs 220 to each other to provide structural support against forces tending to displace the tops of the main springs 220 away from alignment with the longitudinal axis of the lead screws 222. In yet still other cases, the baffle box 204 may also act alone or in combination with other components to hold the spring plate 612 against rotation when the motor 608 is turning the lead screw 222 (e.g., by holding the upper ends of the main springs against rotation).

In some cases the baffle box 204 and slip cover 202 (FIG. 2) are separate components. In other cases, the baffle box 204 is sewn into the slip cover 202 (e.g., the edges that define the top wall 620 are sewn within corresponding locations of the slip cover 202). However, in other cases the functionality of the baffles and the industrial design aspects of the slip cover 202 may be combined into a single component.

As the name implies, each adjustable spring assembly 600 is designed and constructed such that the force carried by each main spring 220 can be adjusted. When the bed controller 118 (FIG. 1) determines a particular adjustable spring assembly 600 should carry more force, the motor 608 is activated to move the spring plate 612 away from the spring rail 200 and toward the sleeping surface 102 (FIG. 1). Moving the spring plate 612 away from the spring rail 200 compresses the main spring 220 and thus the main spring 220 carries more weight or force. Oppositely, when the bed controller 118 determines a particular adjustable spring assembly 600 should carry less force, the motor 600 is activated to move the spring plate 612 toward the spring rail 200 and away from the sleeping surface 102. Moving the spring plate 612 toward the spring rail 200 thus de-compresses the main spring 220 and thus the main spring 220 carries less weight or less force.

While in some embodiments it is possible that the bed controller 118 may control force carried by each adjustable spring assembly 600 in an open-loop sense (e.g., without measuring the weight or force carried by each adjustable spring assembly), in yet still other cases the weight or force carried by each adjustable spring assembly 600 is measured by way of a force sensor. For example, a force sensing mat may be placed over the spring modules 104 after installation. In other cases, each spring module 104 may be associated with a dedicated force sensing mat (e.g., coupled to or forming the upper wall 620 of the baffle box 204). In yet still other cases, each adjustable spring assembly 600 may have an associated force sensor, such as by way of a strain gauge associated with the each motor 608.

Figure 7:
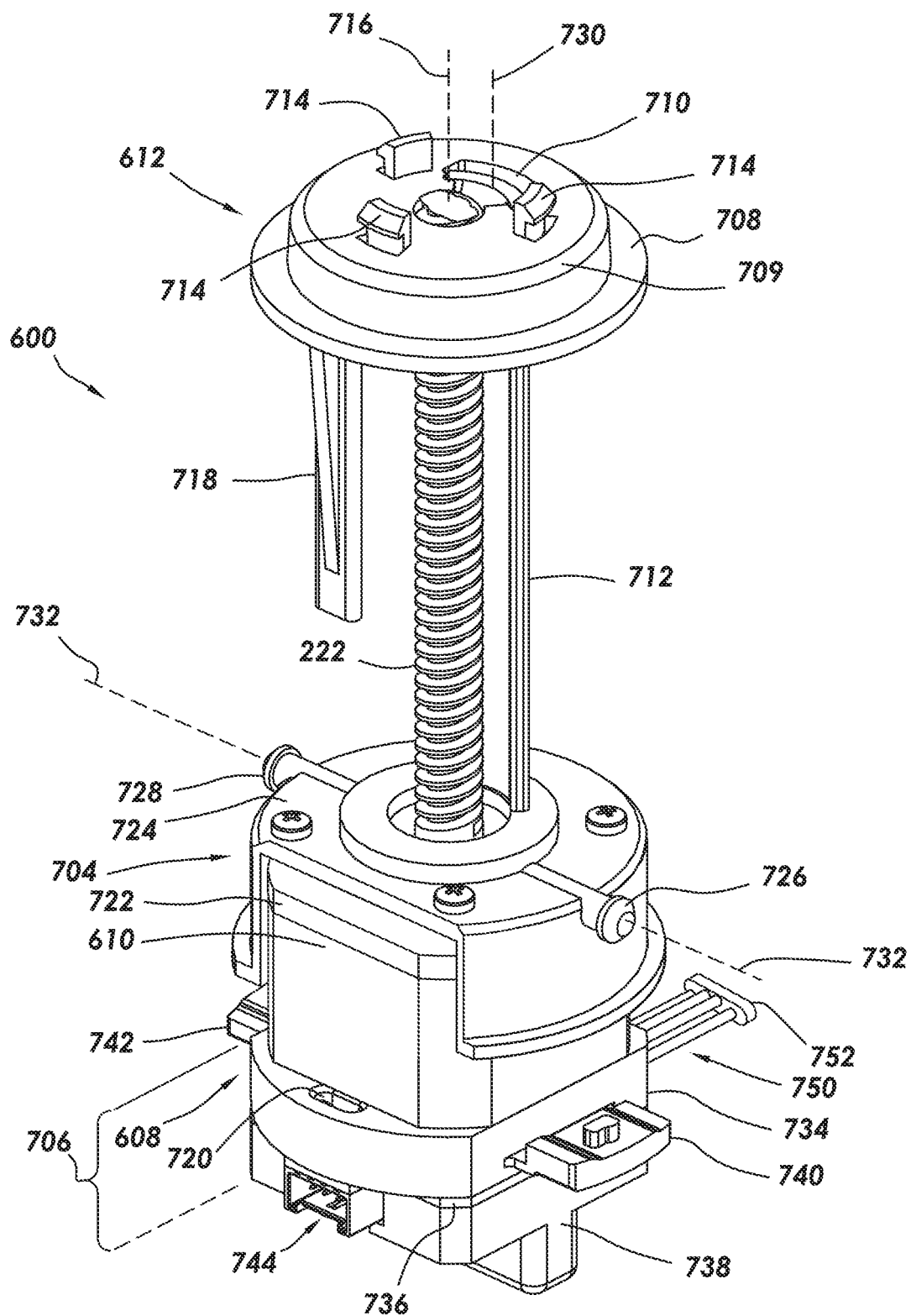
FIG. 7 shows a perspective view of an adjustable spring assembly (without the main spring), and in accordance with at least some embodiments.

FIG. 7 shows a perspective view of an adjustable spring assembly (without the main spring), and in accordance with at least some embodiments. In particular, the example adjustable spring assembly 600 of FIG. 7 shows the motor 608, the lead screw 222, and the spring plate 612. The description turns first to the spring plate 612.

The spring plate 612 is coupled to the lead screw 222 as discussed above, with the precise type of coupling dependent upon how the lead screw 222 couples to the rotor of the motor 608 (e.g., captive and non-captive lead screw). The example spring plate 612 defines an annular shoulder 709 that circumscribes the location of the lead screw 222, and a stop, such as annular flange 708, that extends outward from below the annular shoulder 709. The lower end of the main spring 220 (not shown) couples to the spring plate 612 by telescoping over the annular shoulder 709 and resting on the annular flange 708. The example spring plate 612 further defines an anti-rotation aperture 710 through the spring plate 612 and disposed between the location of the coupling to the lead screw 222 and the annular flange 708. As the name implies, when present the anti-rotation aperture 710 works in conjunction with a post 712 to hold the spring plate 612 against rotation during periods of time when the motor 608 is turning the lead screw 222. The example spring plate 612 further comprises a set of spring clips 714 disposed on and radially spaced around an upper surface of the spring plate 612. FIG. 7 shows three spring clips, but one or more spring clips may be present. The spring clips 714 may be used to hold an additional and optional spring, referred to as a massage spring (discussed in greater detail below). The spring clips 714 are designed and constructed such that as the massage spring is pushed downward over the spring clips 714, the spring clips 714 may deflect slightly inward (e.g., deflect toward a longitudinal central axis 716 of the lead screw 222), and then snap over and hold the wire forming the lower-most loop of wire of the massage spring.

Finally, the example spring plate 612 defines a zero-position post 718. The example zero-position post extends downward from a lower surface of the spring plate 612. In example embodiments, the zero-position post 718 works in conjunction with a micro-switch (exposed through aperture 720, but not visible) to inform the motor controller when the spring plate 612 has reached is lowest or zero position (which may also be a position where the respective main spring carries the least force).

The motor 608 comprises the stator 610 as well as an upper or top plate 704 and a lower or bottom plate 706. The top plate 704 and bottom plate 706 hold the stator 610 together and in place. In the example embodiment of FIG. 7, the top plate 704 is a two-piece component comprising a metallic plate 722 directly abutting the stator 610, and an adapter 724 coupled over and abutting the metallic plate 722. The adapter 724 defines several additional features, such as the post 712 and the protrusions 726 and 728. In other cases, however, the top plate 704 may be an integral component defining all the various features (e.g., post 712 and protrusions 726 and 728). Hereafter, reference will be made to the top plate 704 with the understanding that any feature mentioned may be an integral portion of the top plate 704, or may be implemented by an adapter (e.g., 724) coupled to the top plate 704. The post 712 extends upward from the top plate 704, and a longitudinal central axis 730 of the post 712 is parallel to the longitudinal central axis 716 of the lead screw 222. As noted above, the post 712 works in conjunction with the anti-rotational aperture 710 to help hold the spring plate 612 against rotation, and thus the post 712 may be referred to as an anti-rotation post 712.

Still referring to FIG. 7, the example top plate 704 further includes the buttons or protrusions 726 and 728. In example cases, the protrusions 726 and 728 share a longitudinal central axis 732, and the protrusions 726 and 728 extend outward in opposite directions from the top plate 704. In the example shown, the longitudinal central axis 732 of the protrusions is perpendicular to the longitudinal central axis 716 of the lead screw 222. In some cases, the protrusions 726 and 728 are the locations to which the baffle box 204 (FIG. 6) couples at the location of each adjustable spring assembly 600. In other words, the protrusions 726 and 728 may be the affixation devices 228 shown in FIG. 2. Moreover, as discussed more below, the protrusions 726 and 728 may also act to ensure rotational alignment of the adjustable spring assembly 600 during coupling of the adjustable spring assembly 600 to the respective spring rail 200.

In the example embodiment of FIG. 7, the bottom plate 706 is a multiple-component assembly comprising a mounting plate or suspension member 734, a control PCB 736, and cover piece 738. In example embodiments, the suspension member 734 is metallic and directly abuts the stator 610. The suspension member 734 is associated with a force sensor (not visible in FIG. 7), where the force sensor is configured to measure an amount of weight or force carried by the adjustable spring assembly 600. In particular, the example suspension member 734 defines two ears or tabs 740 and 742. The tabs 740 and 742 extend outward and in the same directions as the example protrusions 726 and 728. When the adjustable spring assembly 600 is coupled to a respective spring rail, the adjustable spring assembly 600 is suspended by the tabs 740 and 742, and more particularly the stator 610 and all the components above the stator are suspended above the tabs 740 and 742. Stated otherwise, when assembled the adjustable spring assembly 600 is rigidly coupled to the spring rail by way of the tabs 740 and 742, and the adjustable spring assembly 600 is suspended above the bottom plate 706.

The example bottom plate 706 further comprises a control PCB 736 sandwiched between the suspension member 734 and the cover piece 738. In example embodiments, electrical connections between various components may be made merely by coupling the three components together. For example, a motor controller disposed on the control PCB 736 may be electrically coupled to electrical pins within a connector (e.g., connector 744) and the windings of the stator 610 of the motor 608 by stacking the three components together. In other cases, the cover piece 738 may be omitted, and the control PCB 736 may be fully or partially exposed on the bottom side of the adjustable spring assembly 600. The electrical aspects of control of the adjustable spring assembly are discussed in greater detail below. Each adjustable spring assembly 600 comprises a pig tail or electrical cable 750 and corresponding electrical connector 752. Thus, the electrical connector 752 is designed and constructed to couple to a corresponding electrical connector 744 of an immediately adjacent adjustable spring assembly 600.

Figure 8:
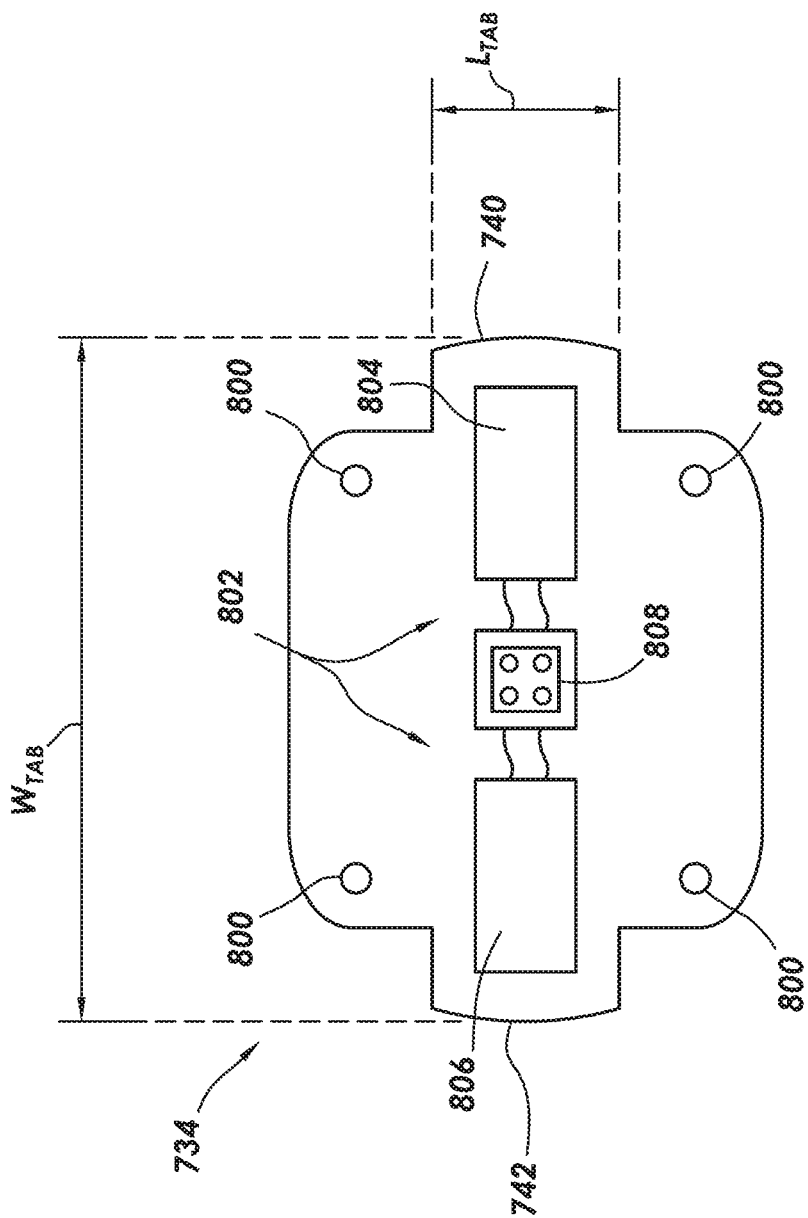
FIG. 8 shows a bottom view of the suspension member in accordance with at least some embodiments.

FIG. 8 shows a bottom view of the suspension member 734 in accordance with at least some embodiments. In particular, the example suspension member 734 includes the tabs 740 and 742 extending outward, along with through bores 800. Affixation devices (e.g., screws) that are not shown extend through the through bores 804 to couple the suspension member 734 to the stator 610 (FIGS. 6 and 7). Within the main body of the suspension member 734 there is a force sensor 802 in the example form a first strain gauge 804 associated with the tab 740 and second strain gauge 806 associated with tab 742. Together the strain gauges 804 and 806 are designed and constructed to measure the weight or force carried by suspension member 734, and thus carried by the adjustable spring assembly 600. More particularly, strain gauge 804 measures strain associated with tab 740, and strain gauge 806 measures strain associated with tab 742. The total weight or force carried may thus be calculated based on the strain associated with tabs 740 and 742. Having two strain gauges is merely an example, and any suitable force sensor that measures weight or force carried may be used. The force sensor 802 is operationally coupled to the bed controller 118 (FIG. 1) by way of the control PCB 736 (FIG. 7). In example embodiments the force sensor 802 electrically couples to the control PCB 736 by way of electrical connector 808. That is, the electrical connector 808 is designed and constructed such that aligning the control PCB 736 with the suspension member 734, and then abutting the control PCB 736 against the suspension member 734, mechanically and electrically couples the electrical connector 808 to a mating connector on the control PCB 736 (the mating connector not shown in FIG. 8). The force sensor 802 (and control PCB 736) provide a value indicative of force to the bed controller 118. Thus, when an adjustable spring assembly 600 is mechanically coupled to a spring rail 200, the force carried by the adjustable spring assembly 600 is measured by the force sensor 802 (and other circuits on the control PCB 736).

The most distal portions of the tabs 740 and 742 define a distance between them, the distance delineated in FIG. 8 as $W_{TAB}$. In example cases, the distance $W_{TAB}$ is greater than a distance between the interior walls of the downwardly projecting legs 402 and 604 of the spring rail 200, where the distance between the interior walls is measured perpendicularly to the length $L_{SR}$ (FIG. 6). Moreover, each of the example tabs 740 and 742 define a tab length delineated in FIG. 8 as $L_{TAB}$. In example cases, the tabs 740 and 742, and the distances $W_{TAB}$ and $L_{TAB}$, play a role in coupling the adjustable spring assembly 600 to a spring rail 200, which in some cases is tool-less operation.

Returning to FIG. 6, and referring to adjustable spring assembly 600A as representative. Coupling adjustable spring assembly 600A involves telescoping the lead screw 222 and spring plate 612 through the first aperture 606A of the spring rail 200, the telescoping from below the spring rail 200 such that the lead screw 222 and spring plate 612 extend above the upper surface 602 of the spring rail 200. Once the lead screw 222 and spring plate 612 are telescoped through the spring rail 200, the example method comprises affixing the motor 608 to the spring rail 200, and coupling the main spring 220 to the spring plate 612. Each adjustable spring assembly 600 is thus coupled in a similar fashion (e.g., telescoping the lead screw and spring plate, affixing the motor, and then coupling the main spring to the spring plate). In the example cases discussed, coupling the main spring 220 occurs after telescoping of the lead screw 222 and spring plate 612 because the largest diameter of the main spring 220 (e.g., at the medial portion) is larger than a usable largest dimension (e.g., diameter) of the aperture 606. However, in cases where the main spring has a diameter smaller than a usable largest dimension of the aperture 606, the main spring 220 may be coupled to the spring plate 612 prior to telescoping the lead screw 222 through the aperture 606, and thus the act of telescoping the lead screw 222 will also telescope the main spring through the aperture 606.

Regardless of the precise order of the steps to get the lead screw 222 and spring plate 612 in the noted orientation, the motor 608 is affixed to the spring rail by being mechanically coupled to the spring rail 200. In at least some example embodiments, affixing the motor 608 to the spring rail 200 comprises rotating the motor 608 relative to the spring rail, the rotation about the longitudinal central axis of the lead screw 222, to engage elements of the suspension member 734 to the spring rail 200. Rotating the motor 608 about the longitudinal central axis of the lead screw 222 may comprise rotating 180 angular degrees or less, in some cases rotating 90 angular degrees or less, and in a particular case rotating 45 angular degrees or less.

Turning again to FIG. 7, and still considering coupling of an adjustable spring assembly 600 to the spring rail 200. When the lead screw 222 and spring plate 612 are telescoped through the aperture 606, the motor 608 and suspension member 734 have a rotational orientation such that the tabs 740 and 742 fit between, and do not interfere with, the downwardly projecting legs 402 and 604 (FIG. 6) of the spring rail 200. Stated otherwise, because the distance $W_{TAB}$ (FIG. 8) between the most distal portions of the tabs 740 and 742 is greater than a distance between the interior walls of the downwardly projecting legs 402 and 604, to telescope the lead screw 222, spring plate 612, and motor 608 through an aperture 606, the motor 608 is placed in a rotational orientation where the distance $W_{TAB}$ forms an acute angle of less than 45 degrees relative to the length $L_{SR}$ of the spring rail 200, and in some cases the distance $W_{TAB}$ is aligned with the length $L_{SR}$ during insertion. Once the lead screw 222, spring plate 612, and at least a portion of the top plate 704 are telescoped through the aperture 606, the motor 608 and suspension member 734 are rotated (e.g., by applying a rotational force to the cover piece 738) such that the tabs 740 and 742 engage with the downwardly projecting legs 402 and 604, respectively.

Figure 9:
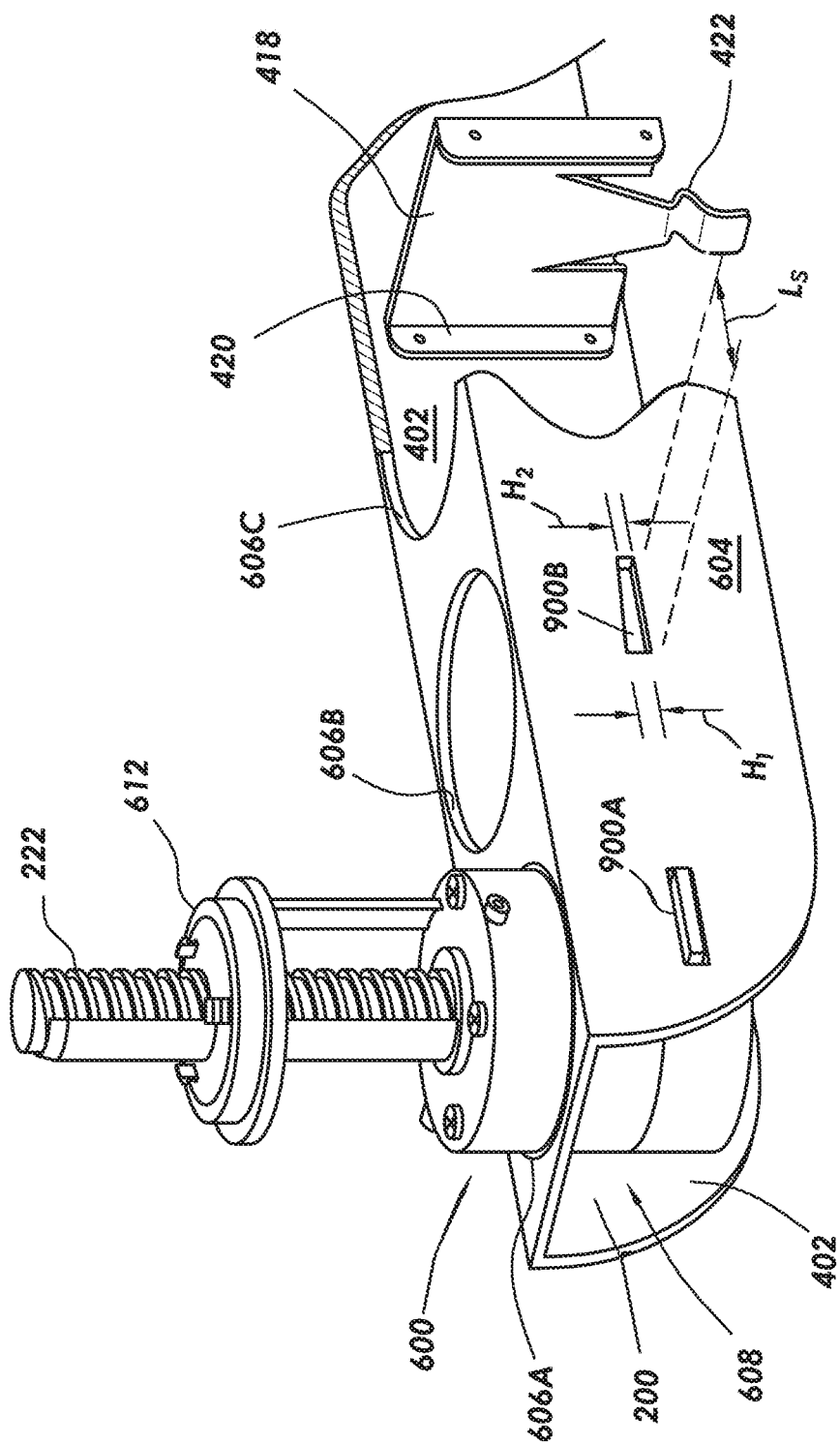
FIG. 9 shows a perspective view of an adjustable spring assembly coupled to a spring rail in accordance with at least some embodiments.

FIG. 9 shows a perspective view of an adjustable spring assembly 600 coupled to a spring rail 200 in accordance with at least some embodiments. In particular, visible in FIG. 9 are a portion of an example spring rail 200, along with a portion of an adjustable spring assembly 600. The portion of the spring rail 200 visible in FIG. 9 includes two full apertures 606A and 606B, and a partial aperture 606C. Aperture 606C is shown in partial cut-away to reveal an example spring latch 418. The example spring latch 418 is coupled to the downwardly projecting leg 402, and would also be coupled to the downwardly projecting leg 604, but a portion of the downwardly projecting leg 604 is also cut away to show the spring latch 418. The example spring latch 418 defines the proximal end 420 coupled to the downwardly projecting leg 402, the coupling by any suitable affixation devices (e.g., screws, rivets, spot welding). Also visible is the ridge 422 designed and constructed to couple over a frame rail (not visible in FIG. 9).

Still referring to FIG. 9, and returning to considerations of the coupling of an adjustable spring assembly 600 to the spring rail 200. The example spring rail 200 defines the downwardly projecting legs 402 and 604. The example downwardly projecting legs 402 and 604 define slots 900 in operational relationship to each aperture 606, though only the slots associated with the downwardly projecting leg 604 are visible in FIG. 9. The number of slots 900 along each downwardly projecting leg 402 and 604 may correspond directly to the number of apertures 606, and thus in some cases between 8 and 40 slots 900 are present along each downwardly projecting leg 402 and 604. FIG. 9 shows and labels the only two slots visible in FIG. 9 (900A and 900B) on downwardly projecting leg 604. Each individual slot 900 will be referred to as "slot 900," and groups of slots will be referred to as "slots 900." The slots 900 are spaced along the length $L_{SR}$ (FIG. 6) of the spring rail 200, and each slot 900 extends from an outer surface of its respective downwardly projecting leg to an inner surface thereof (i.e., the surface facing the opposite downwardly projecting leg). The slots 900 work in conjunction with the tabs 740 and 742 to affix or couple a motor 608 of the adjustable spring assembly 600 to the spring rail 200.

Referring to slot 900B as representative. Representative slot 900B has a length $L_S$, where the length $L_S$ is measured parallel to the length $L_{SR}$ (FIG. 6) of the spring rail 200. The length $L_S$ of the slot 900B is slightly larger than the length $L_{TAB}$ of either tab 740 or tab 742 (FIG. 7). Moreover, the example slot 900B defines two heights, comprising a first height H1 being slightly larger (e.g., between and including 1 to 3 millimeters larger) than height H2. Height H1 is larger than a thickness of the tab 740 or 742, and height H2 is smaller (e.g., equal to the thickness of a tab 740 or 742). The difference in height creates a situation where, as the adjustable spring assembly 600 is turned about the longitudinal central axis of the lead screw 222, the tabs 740 and 742 can only enter the respective slots 900 as the motor 608 is turned in one rotational direction. In the example case of FIG. 9, the tabs 740 and 742 will only protrude into the slots 900 when the motor 608 is turned to the right (when viewed from below). As an adjustable spring assembly 600 is turned to couple or affix the motor 608 to the spring rail, the tabs 740 and 742 protrude into their respective slots 900, with the small height H2 tending to form a friction fit with the respective tab to help hold the tab in the slot 900. When tabs 740 and 742 are coupled within their respective slots and can turn no farther, the rotational orientation defines an installed or locked orientation. Regardless, once installed, the motor 608 (and in particular the suspension member 734) is rigidly coupled to the spring rail 200. Moreover, the example suspension member 734 suspends the motor 608, the lead screw 222, the spring plate 612, and the main spring 220 above the suspension member 734. Thus, slots 900 are examples of a plurality of means for engaging a respective suspension member 734.

The tabs 740 and 742, and corresponding slots 900 in the spring rail, are one example of systems and methods to couple or affix the motor 608 to the spring rail 200. One of ordinary skill in the art, with the benefit of this disclosure, could create many equivalent mechanisms for coupling the motor 608 to the spring rail 200. For example, each downwardly projecting leg could be constructed to create an inwardly projecting ledge (e.g., cutting a "U"-shaped piece and bending the piece inward, or installing ledge member on each downwardly projecting leg), and the suspension member 734 constructed with corresponding slots that interact with the ledges. In yet still other cases, one or more affixation devices (e.g., screws) may be installed through each downwardly projecting leg and into the suspension member 734 to hold the motor 608 in place.

Returning briefly to FIG. 7. In accordance with example systems, each adjustable spring assembly 600 electrically couples to an adjacent or nearest neighbor adjustable spring assembly 600 along a respective shared spring rail 200. In order to reduce the length of electrical cable 750 extending between any two adjustable spring assemblies 600, the adjustable spring assemblies 600 are designed and constructed to couple to the respective spring rail 200 in only one rotational orientation relative to the spring rail 200 about the longitudinal central axis of the lead screw 222. For example, with each adjustable spring assembly 600 coupled in a consistent rotational orientation, the electrical cable 750 of each adjustable spring assembly 600 protrudes or extends from its adjustable spring assembly 600 in the same direction relative to the spring rail 200. The example tabs 740 and 742, by virtue of how the tabs 740 and 742 couple to the respective downwardly projecting legs 402 and 604, limit the affixed relationship of the motor 608 to the spring rail 200 to two rotational orientations, and thus the two rotational orientations result in the possibility of the electrical cable 750 protruding in two opposite directions.

In example embodiments, each spring rail 200 and each adjustable spring assembly 600 implement alignment features that ensure that the motor 608 of the adjustable spring assembly 600 can be coupled or affixed to the spring rail 200 in only one rotational orientation relative to the spring rail (and about the longitudinal central axis of the lead screw 222). In particular, in example systems each aperture 606 of each spring rail 200 has at least one alignment feature, and each top plate 704 of each adjustable spring assembly 600 has at least one corresponding or complementary alignment feature, that ensures that the top plate 704 can telescope through an aperture 606 in only one rotational orientation. In some cases, once the alignment features clear each other, the adjustable spring assembly 600 may be free to rotate, but the tabs 740 and 742 and slots 900 limit further rotation.

FIG. 10 shows an exploded, partial perspective, and partial cut-away, view of an adjustable spring assembly 600 and spring rail 200 in accordance with at least some embodiments. In the example of FIG. 10, the alignment features are shown as protrusions from the top plate 704 (e.g., protrusions from the adapter 724), and corresponding notches in the aperture 606. In particular, the example top plate 704 defines three protrusions. The first two protrusions are protrusions 726 and 728, and thus the protrusions 726 and 728 serve double duty in the example system, being used both as alignment features for telescoping the motor 608 through the aperture 606, and to couple to the pockets defined by the baffle box 204. Inasmuch as the two protrusions 726 and 728 share a central axis 732, in order to ensure that the top plate 704 will telescope through the aperture 606 in only one rotational orientation, a third alignment feature in the form of a ridge 1000 is also defined by the top plate 704. The example ridge 1000 has a rectangular cross-section, and is positioned at a radial location centered between the radial locations of the protrusions 726 and 728. However, in other cases the ridge 1000 may be placed at any suitable radial location, and the ridge may take any suitable cross sectional shape (e.g., square or triangular). Having three example protrusions thus limits the rotational orientations that the top plate 704, and thus the motor 608, will telescope through the aperture 606 to a single telescoping rotational orientation. In case where the protrusions 726 and 728 are omitted, a single protrusions may be sufficient to ensure proper rotational alignment.

FIG. 10 further shows a portion of an example spring rail 200, including a single aperture 606. It is noted, however, that given the modular character of the adjustable spring assemblies 600, correspondingly some or all the apertures 606 in a spring rail 200 may be identical. The example aperture 606 defines alignment features in the form of notches 1002, 1004, and 1006. Notch 1002 corresponds to protrusion 728. Notch 1004 corresponds to ridge 1000. And notch 1004 corresponds to protrusion 726. Thus, as the top plate 704 is telescoped through the aperture 606, the protrusions move through their respective notches, forcing rotational alignment of the top plate 704 to only one rotational orientation. In accordance with example embodiments, the protrusions 726, 728, and 1000 have a height (measured parallel to the longitudinal central axis 716 of the lead screw 222) less than a distance D between the protrusions and the tabs 740 and 742. Thus, once the protrusions clear the upper surface 602 of the spring rail 200, the top plate 704 and motor 608 may again rotate about the longitudinal central axis 716 of the lead screw 222 to enable the tabs 740 and 740 to couple into the slots 900. However, in other cases, the one or more alignment features associated with the motor 608 may limit rotation any time the top plate 704 is telescoped through the aperture 606 (e.g., when the motor 608 is affixed to the spring rail 200 by affixation devices such as screws or rivets).

While the top plate 704 shown in FIG. 10 defines the alignment features as protrusions, and while the aperture 606 defines the alignment features as notches, the distribution of the alignment features is not so limited. For example, in other cases the aperture 606 may have inward facing ridges while the top plate 704 (e.g., adapter 724) has corresponding notches. Moreover, the alignment features with respect to the top plate 704 need not be consistent. For example, the top plate 704 may have one or more protrusions and one or more notches, and the aperture 606 will thus have one more corresponding ridges and one or more corresponding notches. In any event, the alignment features are used to limit rotational alignment during telescoping of the top plate and motor 608 through the spring rail 200.

As alluded to with respect to FIGS. 7 and 10, each adjustable spring assembly 600 comprises a control PCB 736 both mechanically and electrically coupled to the motor 608. The control PCB 736 further communicatively couples (e.g., electrically, optically) to other control PCBs in other adjustable spring assemblies along a spring rail, and also communicatively couples to the bed controller 118 (FIG. 1).

The specification thus turns to example components that may be disposed on the control PCB 736 of each adjustable spring assembly 600.

Figure 11:
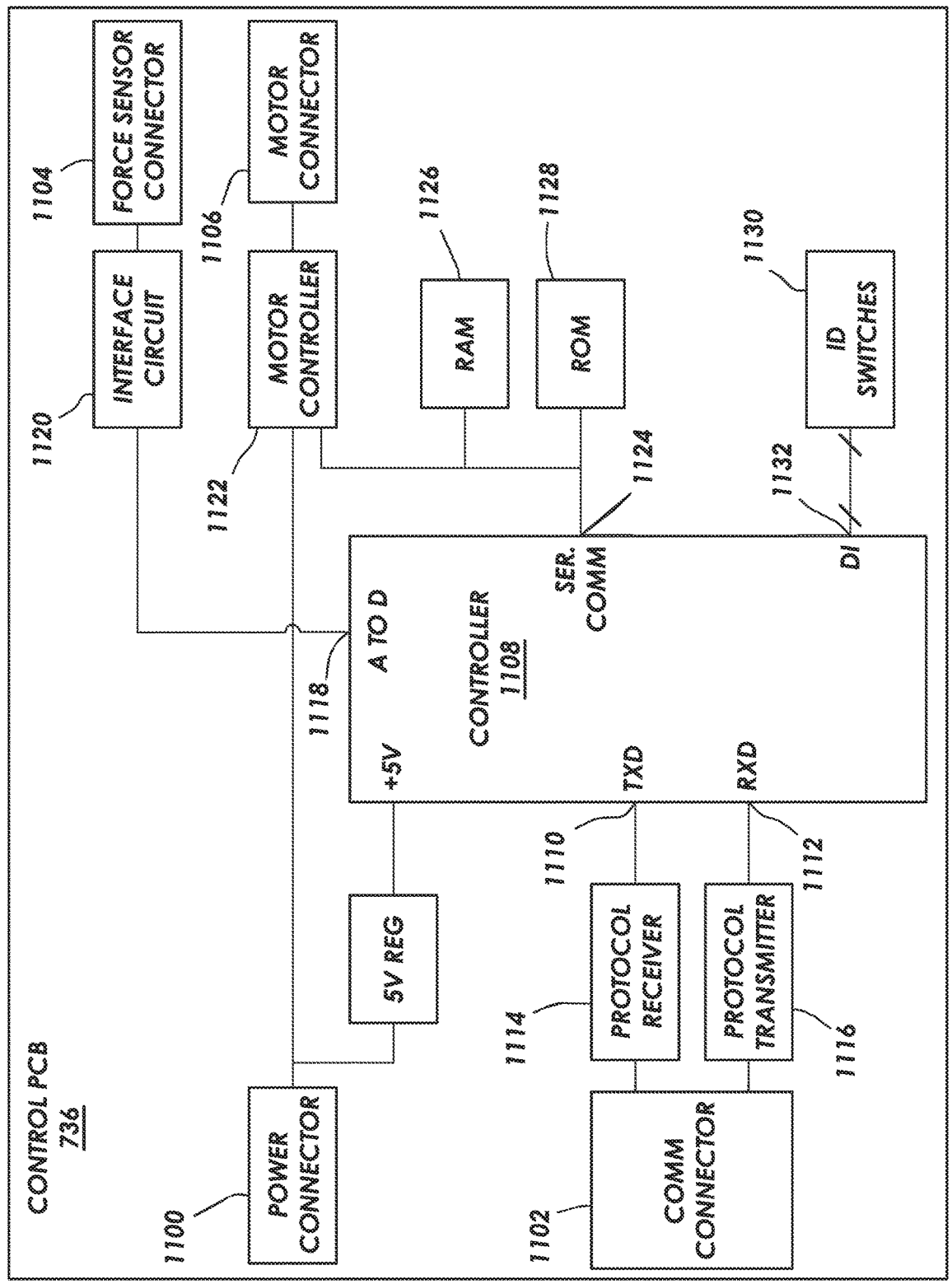
FIG. 11 shows a block diagram of the control PCB in accordance with at least some embodiments.

FIG. 11 shows an electrical block diagram of the control PCB in accordance with at least some embodiments. In particular, the example control PCB 736 interfaces with components of the control PCB 736 by way of a plurality of connectors, such as power connector 1100, communication connector 1102, force sensor connector 1104, and motor connector 1106. The power connector 1100 may couple to both upstream and downstream adjustable spring assemblies, and thus may be electrically connected to both the externally accessible electrical connector 744 (FIG. 7) and electrical cable 750 (FIG. 7). In example cases, the control PCB 736 is provided DC power (e.g., 12 VDC) to power the various components on the control PCB 736. Similar to the power connector 1100, the communication connector 1102 may couple to both upstream and downstream adjustable spring assemblies, and thus may be electrically connected to both the externally accessible electrical connector 744 (FIG. 7) and electrical cable 750 (FIG. 7). The force sensor connector 1104 is designed and constructed to couple the mating electrical connector 808 (FIG. 8) associated with the force sensor 802 (also FIG. 8). And finally, the motor connector 1106 is designed and constructed to couple to the winding or windings disposed within the stator 610 of the motor 608 (both FIG. 6).

In example systems, each control PCB 736 includes a controller 1108 (e.g., a PIC16F19155 microcontroller available from Microchip Technology Inc. of Chandler, Ariz.). The example controller 1108 defines a plurality of input and output ports. For example, the controller 1108 defines a transmit port 1110 and a receive port 1112. In the example system, the transmit port 1110 couples to a protocol receiver 1114, and the receive port 1112 couples to a protocol transmitter 1116. In example systems, the protocol receiver 1114 and the protocol transmitter 1116 implement a communication protocol, such as an Institute of Electrical and Electronics Engineers (IEEE) RS485 serial communication protocol. By way of the communication protocol, the bed controller 118 (FIG. 1) may command the controller 1108 to take action, such as increasing or decreasing the weight or force carried by the adjustable spring assembly 600 within which the controller 1108 is implemented.

The controller 1108 further includes an analog-to-digital (A/D) input port 1118. In the example system, the ND input port 1118 may be used to read values indicative of force from the force sensor 802. In particular, the example system comprises an interface circuit 1120 electrically disposed between the ND input port 1118 and the connector 1104 (and thus the force sensor 802). The interface circuit 1120 may implement circuits used to power and/or read the force sensor 802. The precise nature of the interface circuit 1120 depends on the type of force sensor implemented. In an example case the interface circuit 1120 implements a differential amplifier, with the type of differential amplifier dependent upon the precise nature of the force sensor 802. While in the example system the interface circuit 1120 couples to the controller 1108 by way the A/D input port 1118, other communication systems may be used (e.g., serial interface).

Still referring to FIG. 11, the example control PCB 736 further comprises a motor controller 1122. The motor controller 1122 is electrically coupled to, and receives power from, the power connector 1100. The motor controller 1122 couples to the motor connector 1106, and thus when assembled into an adjustable spring assembly 600 the motor controller 1122 couples to the winding or windings of the motor 608. The precise nature of the motor controller 1122 depends on the type of motor 608 implemented within the adjustable spring assembly 600.

The controller 1108 defines a serial communication port 1124, and in the example system the controller 1108 communicates with the motor controller 1122 over the serial communication port 1124. The serial communication port 1124, and related protocol, may take any suitable form (e.g., a serial peripheral interface (SPI)). In other cases, the controller 1108 may be communicatively coupled to the motor controller 1122 by any suitable communication systems, including by sending and/or receiving analog signals to the motor controller 1122.

The controller 1108 in some cases has onboard random access memory (RAM) and non-volatile storage (e.g., read-only member (ROM)), but in the example system the controller PCB 736 also implements external RAM 1126 and external ROM 1128. The example RAM 1126 and ROM 1128 are communicatively coupled to the controller 1108 by way of the serial communication port 1124, but any suitable communication system and protocol may be used. The RAM 1126 may be used to store programs executed by a processor of the controller 1108 (the processor not specifically shown), and in some cases the RAM 1126 may be the working memory for the controller 1108. Further still, the RAM 1126 itself may implement a non-volatile aspect (e.g., the RAM 1126 may be static RAM (SRAM)). The ROM 1128 may likewise be used to store programs executed by a processor of the controller 1108, including the underlying operating system and basic input-output system (BIOS) services. The ROM 1128 may take any suitable form, such as an electrically-erasable programmable ROM (EEPROM).

Still referring to FIG. 11, the example control PCB 736 further comprises a set of identification switches 1130 coupled to the controller 1108. In particular, in the example system the controller 1108 defines a plurality of digital inputs 1132. By way of the digital inputs 1132, the controller 1108 may read the on/off state of each switch of the identification switches 1130. Using the identification switches 1130, the controller 1108, and thus the control PCB 736 and overall adjustable spring assembly, can be uniquely identified by the bed controller 118. In other cases, however, identification of each adjustable spring assembly may take place programmatically (e.g., reading a unique media access control (MAC) address from each control PCB), and thus the identification switches 1130 may be omitted, or used for other functions. For example, the switches may be used to identify membership in a particular adjustable spring module 104, or the switches may be used to identify the first adjustable spring assembly in a spring module 104 when the communication protocol relies on communicatively daisy-chaining of the adjustable spring modules 600.

Figure 12:
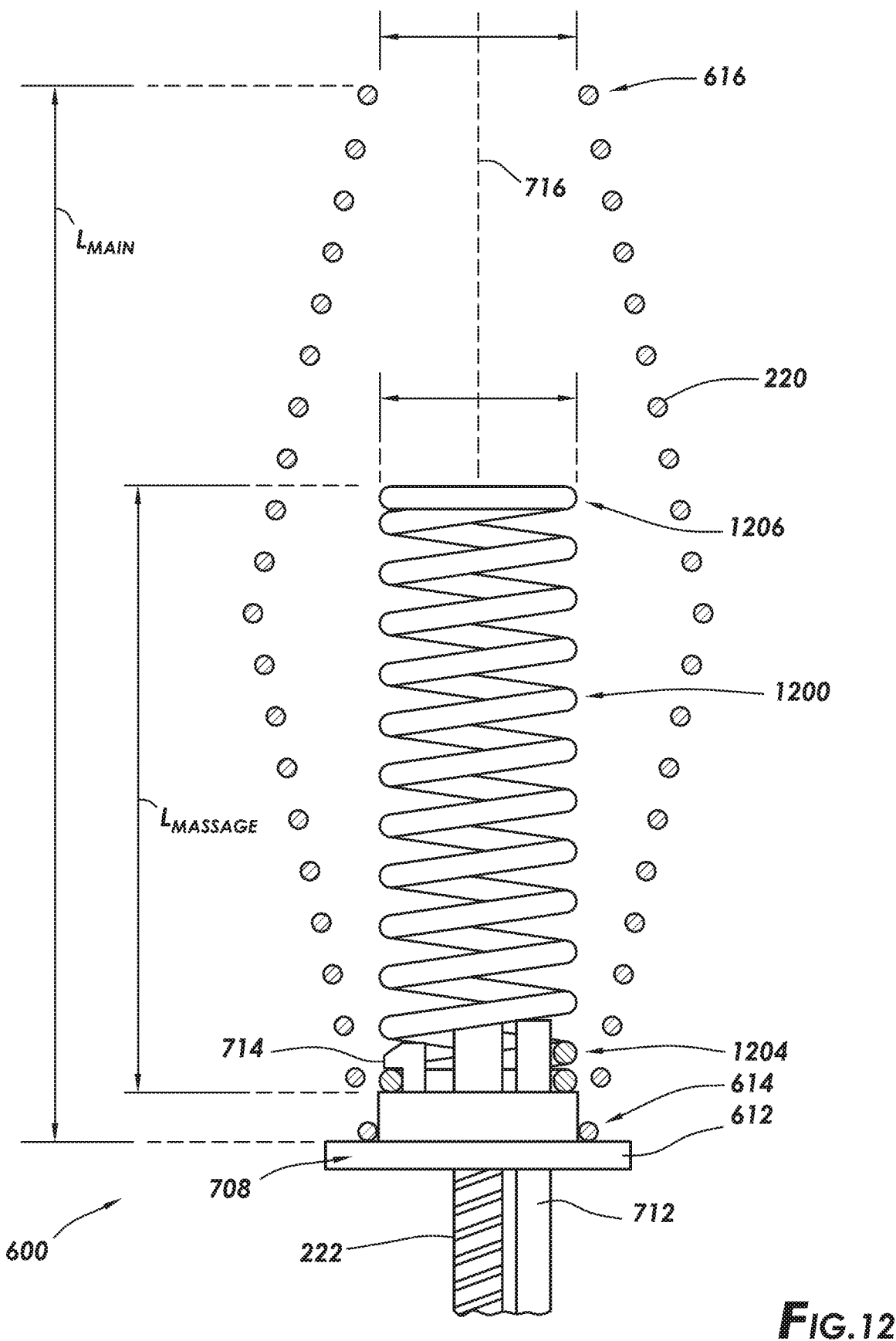
FIG. 12 shows a side elevation, partial cross-sectional view, of a portion of an adjustable spring assembly in accordance with at least some embodiments.

FIG. 12 shows a side elevation, partial cross-sectional view, of a portion of an adjustable spring assembly in accordance with at least some embodiments. In particular, shown in FIG. 12 is a side elevation view of the spring plate 612 coupled to the lead screw 222 and in operational relationship to the post 712. The components of the adjustable spring assembly below the lead screw 222 and post 712 are omitted to provide further detail regarding the springs. In at least some embodiments the adjustable spring assemblies 600 comprise two springs—a main spring 220 and a massage spring 1200. In FIG. 12, the main spring 220 is shown in cross-section to reveal the internal massage spring 1200. The main spring 220 is a helical spring that couples on the first end 614 by telescoping over the spring plate 612 and resting on the annular flange 708. The lead screw 222 defines a longitudinal central axis 716. The main spring 220, in spite of being barrel shaped, has a central axis that is coaxial with the longitudinal central axis 716. The optional massage spring 1200 defines a central axis that is coaxial with the central axis of the main spring 220, and thus coaxial with the longitudinal central axis 716 of the lead screw 222. In other cases, however, the massage spring 1200 may be shifted such that the central axis of the massage spring 1200 is parallel to, but not coaxial with, the remaining central axes.

The massage spring 1200 defines a lower end 1204 and an upper end 1206. The lower end 1204 in the example systems is coupled to the spring plate 612 by way of the spring clips 714. Only one spring clip 714 shown in FIG. 12, but more than one may be used. It is noted that the lower end 1204 of the massage spring 1200 is also shown in partial cross-section to illustrate the spring clip 714 clipping over and holding the lower end 1204 against the upper surface of the spring plate 612. As illustrated by FIG. 12, the main spring 220 defines an un-laden length $L_{MAIN}$, with the length as discussed above. The massage spring 1200 likewise defines an un-laden length $L_{MASSAGE}$ that is less than the $L_{MAIN}$. When the length $L_{MAIN}$ is about 10 inches, the length $L_{MASSAGE}$ may be between and including 4 inches and 8 inches, and in some cases between and including 5 inches and 6 inches. In some cases, the massage spring 1200 has spring constant greater than the spring constant of the main spring 220, but in other cases the spring constant of the massage spring 1200 may be the same or smaller than the spring constant of the main spring 220. In accordance with example systems, the massage spring 1200 is used in conjunction with movement of the spring plate 612 to implement an additional massage function for the overall adjustable sleeping system 100 (FIG. 1). In particular, under command of the bed controller 118 (FIG. 1), the adjustable spring assembly 600 may quickly drive the spring plate 612 upward to fully compress the main spring 220, and thus enabling the upper end 1206 of the massage spring 1200 to extend at least to the second end 616 of the main spring 220, and in some cases extend above the second end 616 of the main spring 220, to provide a more concentrated force to the body of the user of the adjustable sleeping system 100. It follows that the spring constant of the massage spring 1200 is higher than the spring constant of the main spring 220.

Commercially available beds differ in many respects, but the primary differentiator is firmness. The measure of firmness differs by manufacturer, but in most cases firmness is judged along a spectrum from very soft (sometimes "extra plush") to extra firm. The example adjustable sleeping system 100 may emulate the entire firmness range. In particular, for a very soft setting the bed controller 118 may command all the adjustable spring assemblies 600 to retract their respective spring plates 612 to the position closest to the respective motors 608 (e.g., the zero position discussed above). Thus, the user of the bed takes advantage of the lower spring constant of the main spring 220. Oppositely, for a very firm setting the bed controller 118 may command the adjustable spring assemblies 600 to move their respective spring plates 612 to the position closest to the second ends 616 of the main spring 220. As discussed above, the pockets of the baffle box 204 and/or the slip cover 202 limit spring travel, and thus the springs are partially compressed against the baffle box 204. Thus, for a firm or extra firm setting the user of the bed takes advantage of the main spring 220 being fully compressed and/or the extra support of the massage spring 1200.

While possible that the adjustable spring assemblies 600 could be used solely to implement firmness across the entire bed, the individually addressable and controlled adjustable spring assemblies 600 provide better granularity. In particular, in addition to or in place of the firmness adjustability, example embodiments implement any of a number of force control and/or normalization routines to lower the force applied to any particular portion of the user's body.

Figure 13:
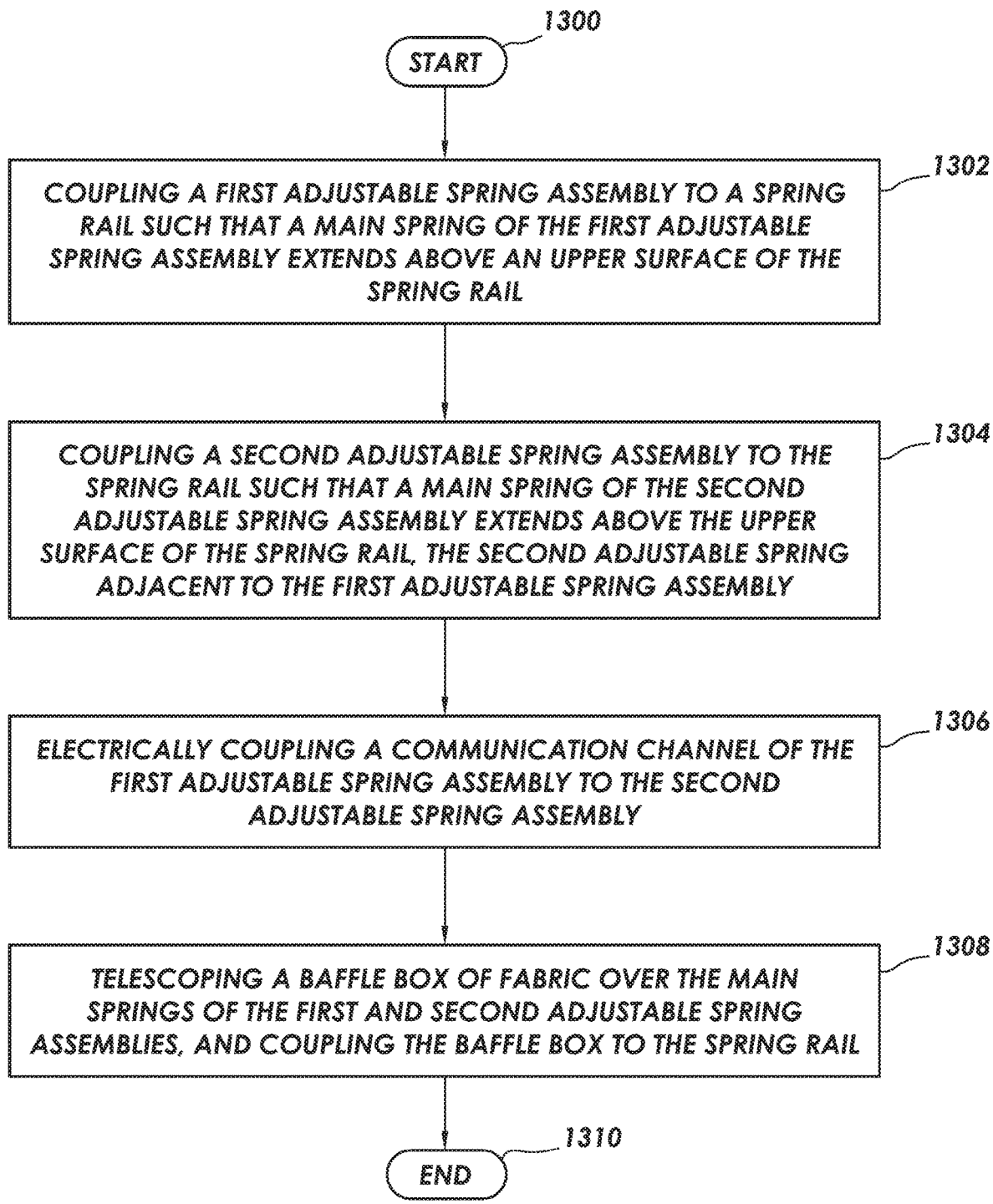
FIG. 13 shows a method of assembly of a spring module for an adjustable sleeping system, and in accordance with at least some embodiments.

FIG. 13 shows a method of assembly of a spring module 104 for an adjustable sleeping system 100, and in accordance with at least some embodiments. The method starts (block 1300) and comprises: coupling a first adjustable spring assembly 600 to a spring rail 200 such that a main spring 220 of the first adjustable spring assembly 600 extends above an upper surface of the spring rail 200 (block 1302); coupling a second adjustable spring assembly 600 to the spring rail 200 such that a main spring 220 of the second adjustable spring assembly 600 extends above the upper surface of the spring rail 200, the second adjustable spring 600 adjacent to the first adjustable spring assembly 600 (block 1304); electrically coupling a communication channel of the first adjustable spring assembly 600 to the second adjustable spring assembly 600 (block 1306); and telescoping a baffle box 204 of fabric over the main springs 220 of the first and second adjustable spring assemblies 600, and coupling the baffle box 204 to the spring rail 200 (block 1308). Thereafter the method ends (block 1310), to be restarted for coupling of the next adjustable spring assembly 600.

The above discussion is meant to be illustrative of the principles and various embodiments of the present invention. Numerous variations and modifications will become apparent to those skilled in the art once the above disclosure is fully appreciated. For example, an overall bed may be conceptually (though not necessarily physically) divided such that two users could individually control their respective sides. Including individual control of firmness, massage, force normalization, spine alignment and/or any other function implemented by the bed system. It is intended that the following claims be interpreted to embrace all such variations and modifications.

What is claimed is:

1. A spring module for an adjustable sleeping system, comprising:
    a spring rail that defines a length, a width, an upper surface, and a lower surface, the spring rail having a plurality of apertures extending between the upper surface and the lower surface along the length;
    a plurality of adjustable spring assemblies spaced along the length of the spring rail;
    each adjustable spring assembly comprises:
        a motor with a stator and a rotor, the motor coupled to the spring rail within one of the plurality of apertures;
        a lead screw coupled to the rotor and extending above the upper surface;
        a spring plate coupled to the lead screw for translation along the lead screw away from the spring rail in response to rotation of the lead screw in a first direction and for translation along the lead screw toward the spring rail in response to rotation of the lead screw in a second direction opposite the first direction; and
        a main spring having a first end coupled to the spring plate, the main spring extending away from the spring plate to a second end opposite the first end, wherein the main spring is configured to be compressed in response to the spring plate translating along the lead screw away from the spring rail, and to be de-compressed in response to the spring plate translating along the lead screw toward the spring rail.

2. The spring module of claim 1 wherein each adjustable spring assembly further comprises a force sensor associated with the stator, the force sensor configured to measure an amount of force carried by the respective adjustable spring assembly.

3. The spring module of claim 1 wherein each adjustable spring assembly further comprises:
    a bottom plate coupled to the stator of the motor, the bottom plate rigidly coupled to the spring rail; and
    a force sensor in operational relationship to the bottom plate and the spring rail, the force sensor configured to measure an amount of force carried by the respective adjustable spring assembly.

4. The spring module of claim 3 wherein each adjustable spring assembly further comprises the bottom plate coupled to the spring rail, and the motor, lead screw, spring plate, and main spring suspended above the bottom plate.

5. A spring module for an adjustable sleeping system, comprising:
    a spring rail that defines a length, a width, an upper surface, a lower surface, and a plurality of apertures along the length, each aperture of the plurality of apertures extends between the upper surface and the lower surface, each aperture of the plurality of apertures defining a first alignment feature;
    a plurality of adjustable spring assemblies spaced along the length of the spring rail, each adjustable spring assembly comprising:
        a motor with a stator and a rotor, the motor coupled to the spring rail;
        a lead screw coupled to the rotor and extending above the upper surface;
        a top plate coupled to the stator of the motor, the top plate defining a second alignment feature configured to enable the top plate to telescope through a respective aperture in only one rotational orientation relative to the spring rail about a longitudinal central axis of the lead screw;
        a spring plate coupled to the lead screw; and
        a main spring having a first end coupled to the spring plate, and a second end opposite the first end.

6. The spring module of claim 5:
    wherein the first alignment feature further comprises a notch at a radial location of the respective aperture;
    wherein the second alignment feature further comprises a protrusion from the top plate at a radial location of the respective top plate such that the top plate telescopes through a respective aperture in only one rotational orientation.

7. The spring module of claim 6 further comprising a baffle box of fabric, the baffle box comprising:
    a top wall, a first side wall, a second side wall, a first end wall, a second end wall, and an interior volume;
    a plurality of baffles within the interior volume, each baffle of the plurality of baffles extends between the first side wall and the second side wall, the plurality of baffles define a plurality of pockets within the baffle box;
    each pocket of the baffle box telescoped over a respective main spring of a respective adjustable spring assembly; and each pocket of the baffle box coupled on a lower end to the protrusion of the respective top plate.

8. The spring module of claim 5:
wherein each adjustable spring assembly further comprises a bottom plate coupled to the stator of the motor, and the bottom plate defining a means for locking the bottom plate to the spring rail;
wherein the spring rail further comprises:
- a first side wall along the length and extending downward;
- a plurality of first means for engaging a respective bottom plate, each first means for engaging associated with the first side wall, and each first means for engaging associated with a respective aperture of the plurality of apertures;

wherein each adjustable spring assembly has two rotational orientations relative to a respective aperture about the longitudinal central axis of the lead screw with, the two rotational orientations comprising: a first rotational orientation being the only one rotational orientation and in which the means for engaging is unengaged with the bottom plate; and a second rotational orientation in which the means for engaging is engaged with the bottom plate.

9. The spring module of claim 1:
wherein each adjustable spring assembly further comprises a top plate coupled to the stator of the motor, the top plate extends above an upper surface of the spring rail;
wherein the spring module further comprises a baffle box of fabric, the baffle box comprising:
- a top wall, a first side wall, a second side wall, a first end wall, a second end wall, and an interior volume;
- a plurality of baffles within the interior volume, each baffle of the plurality of baffles extends between the first side wall and the second side wall, the plurality of baffles define a plurality of pockets within the baffle box;
- each pocket of the baffle box telescoped over a respective main spring of a respective adjustable spring assembly; and
- each pocket of the baffle box coupled on a lower end to the respective top plate.

10. The spring module of claim 1 wherein each adjustable spring assembly further comprises a massage spring coupled to the spring plate, the massage spring coaxial with the main spring, and the massage spring has a higher spring constant than the main spring.

11. The spring module of claim 1 wherein each adjustable spring assembly further comprises:
- a top plate coupled to the stator of the motor, the top plate having an anti-rotation post that extends upward from the top plate, a longitudinal central axis of the anti-rotation post parallel to a longitudinal central axis of the lead screw;
- an anti-rotation aperture through the spring plate, the anti-rotation post telescopes through the anti-rotation aperture.

12. The spring module of claim 1 further comprising a baffle box comprising:
- a lower end coupled to the spring rail and opposite side walls extending upwardly from the lower end to a top wall,
- wherein the second end of the main spring abuts the top wall of the baffle box, such that top wall restricts travel of the main spring,
- wherein a height of the main spring is decreased upon the second end of the main spring being compressed against the top wall of the baffle box in response to the spring plate translating along the lead screw away from the spring rail.

13. The spring module of claim 12 wherein the baffle box further comprises:
- a plurality of baffles extending between the opposite side walls, the plurality of baffles define a plurality of pockets within the baffle box; and
- each pocket of the baffle box containing a respective main spring of a respective adjustable spring assembly therein.

14. The spring module of claim 13 wherein the baffle box is fabric.

* * * * *